(12) United States Patent
Otto et al.

(10) Patent No.: US 6,660,835 B1
(45) Date of Patent: Dec. 9, 2003

(54) LEAD SUBSTANCES AND THEIR USE AS THERAPEUTICS

(75) Inventors: Michael Otto, Tuebingen (DE); Roderich Suessmuth, Nuertingen (DE); Guenther Jung, Tuebingen (DE); Friedrich Goetz, Beim Herbstenhof 31 D- 72076, Tuebingen (DE)

(73) Assignee: Friedrich Goetz, Tuebingen (DE)

( * ) Notice: Subject to any disclaimer, the term of this patent is extended or adjusted under 35 U.S.C. 154(b) by 0 days.

(21) Appl. No.: 09/219,865

(22) Filed: Dec. 24, 1998

(51) Int. Cl.⁷ ................................................ A61K 38/08
(52) U.S. Cl. ........................ 530/329; 530/300; 530/317
(58) Field of Search ............................... 536/23.1, 23.7; 530/300, 317, 328, 329; 514/15, 16, 44

(56) References Cited

PUBLICATIONS

Mahony et al. (PNAS vol. 92, pp. 6474–6478, 1995).*
Fleischmann et al. (Science Vol 269 pp. 496–512, 1995).*
Van Wamel et al. (FEMS Microbiology Letters vol. 163 pp. 1–9, 1998).*
Novick et al., EMBO Journal, vol. 12, No. 10, pp. 3967–3975 (1993).
Novick et al., Mol. Gen. Genet., 248: 446–458 (1995).
Michael Otto et al., FEBS Letters, 424, pp. 89–94 (1998).
Mayville et al., Proc. Natl. Acad. Sci. USA, 96: 1218–1223 (1999).

* cited by examiner

*Primary Examiner*—Lynette R. F. Smith
*Assistant Examiner*—Robert A. Zeman
(74) *Attorney, Agent, or Firm*—Birch, Stewart, Kolasch & Birch, LLP

(57) ABSTRACT

The present invention relates to peptides, which are useful in treating Staphylococcus infections. More particularly, the inventive peptides interfere with the regulation of the agr system of Staphylococcus species, especially S. aureus, and thereby block the formation of different virulence factors. The inventive peptides comprise at least the amino acid sequence S V X A S Y F, whereby cyclic structures of that kind of peptides are the most potent blocking reagents.

16 Claims, 16 Drawing Sheets

```
  1 TTATATTTTT TTAACATTAC GTACTGAAGC GAAACAATTT TCGCCATTCT TAAAGTAAAC
    AATATAAAAA AATTGTAATG CATGACTTCG CTTTGTTAAA AGCGGTAAGA ATTTCATTTG
     *  I  K  K   V  N  R   V  S  A   F  C  N  E   G  N  K   F  Y  V

61 AATACGTTCT TTGAGTCAA TAGATTCAAT ATTATGCCTG TTTATTACAA AACTGTTATG
    TTATGCAAGA AACTCAGTT ATCTAAGTTA TAATACGGAC AAATAATGTT TTGACAATAC
     I  R  E  K   S  D  I   S  E  I   N  H  R  N   I  V  F   S  N  H

121 ACATCTAAAG AAACGTTCAT CAAGCTGTGC TAATTCCTTT AAATTTCCAT AAAATTCAAT
    TGTAGATTTC TTTGCAAGTA GTTCGACACG ATTAAGGAAA TTTAAAGGTA TTTTAAGTTA
     C  R  F  F   R  E  D   L  Q  A   L  E  K  L   N  G  Y   F  E  I

181 TTGTCGATTA TCAAGATGTG CAATGAGTCT ATGAGATTTC GTAGATGATT CAAAAAACAT
    AACAGCTAAT AGTTCTACAC GTTACTCAGA TACTCTAAAG CATCTACTAA GTTTTTTGTA
     Q  R  N  D   L  H  A   I  L  R   H  S  K  T   S  S  E   F  F  M

241 AATATCATCA TATTGAACGT ATACTGAATT ACTTCCCCGC TTTAACTCAA TCGTATCTAC
    TTATAGTAGT ATAACTTGCA TATGACTTAA TGAAGGGGCG AAATTGAGTT AGCATAGATG
     I  D  D  Y   Q  V  Y   V  S  N   S  G  R  K   L  E  I   T  D  V

301 ATTACTTTCT TTTGATAATA ATTTGAGTCT TGTATGTGCT GTTTCAAGAC AATCTATGAT
    TAATGAAAGA AAACTATTAT TAAACTCAGA ACATACACGA CAAAGTTCTG TTAGATACTA
     N  S  E  K   S  L  L   K  L  R   T  H  A  T   E  L  C   D  I  I

361 TCTCATTTTT AATTCAGATG GATCATCTTT AAAAATAAAA TCCATAGCAG CCACTTTATA
    AGAGTAAAAA TTAAGTCTAC CTAGTAGAAA TTTTTATTTT AGGTATCGTC GGTGAAATAT
     R  M  K  L   E  S  P   D  D  K   F  I  F  D   M  A  A   V  K  Y

421 AACAAACGTC AAATAAGTCA GCTCACTGTG ACTGGTTACA AATATAATAT TACCAACAGG
    TTGTTTGCAG TTTATTCAGT CGAGTGACAC TGACCAATGT TTATATTATA ATGGTTGTCC
     V  F  T  L   Y  T  L   E  S  H   S  T  V  F   I  I  N   G  V  P

481 ATCATGTTTA CGAATTTCAC TGGCTAATTT AATACCGTTC ATATCAGCTT CTAATTGAAT
    TAGTACAAAT GCTTAAAGTG ACCGATTAAA TTATGGCAAG TATAGTCGAA GATTAACTTA
     D  H  K  R   I  E  S   A  L  K   I  G  N  M   D  A  E   L  Q  I

541 ATCAAGGAAG TAACAACCAA TGTCATTAAG TTCTTTTGAT TGCTCTAAGA CCTCATAAGG
    TAGTTCCTTC ATTGTTGGTT ACAGTAATTC AAGAAAACTA ACGAGATTCT GGAGTATTCC
     D  L  F  Y   C  G  I   D  N  L   E  K  S  Q   E  L  V   E  Y  P

601 ATCATTTGTT CGTAAAGCTA ACTCCATTGG CTTTTCTTCA ATCATTATGT AGTTTTTAAT
    TAGTAAACAA GCATTTCGAT TGAGGTAACC GAAAAGAAGT TAGTAATACA TCAAAAATTA
     D  N  T  R   L  A  L   E  M  P   K  E  E  I   M  I  Y   N  K  I

661 GATTGATACC ATATGTTCTC TTTGTCTTTG GTCATCTTCA CAAACAAAAA TTTTCATTTA
    CTAACTATGG TATACAAGAG AAACAGAAAC CAGTAGAAGT GTTTGTTTTT AAAAGTAAAT
     I  S  V  M   H  E  R   Q  R  Q   D  D  E  C   V  F  I   K  M agrA 721 ATTCTACACA TCCTTATGAT TCCTTATTAT TTATTTCTAC TTTTTGTACA AAGTAACCAT
    TAAGATGTGT AGGAATACTA AGGAATAATA AATAAAGATG AAAAACATGT TTCATTGGTA
         *  S  E   K  N  N   I  E  V   K  Q  V   F  Y  G  N
```

FIG.1A-1

```
781   TTTCGATGAC AGTATCTAAT AAAACATTCT CGTTTGAGTC TGTCAGTTCT TTTAAAGTTG
      AAAGCTACTG TCATAGATTA TTTTGTAAGA GCAAACTCAG ACAGTCAAGA AAATTTCAAC
       E   I   V   T   D   L   L   V   N   E   N   S   D   T   L   E   K   L   T   S

841   ATAAACCTAA ACCGCGATTA TCACCTTTAG TAGAAAAACC TTGTTCAAAC AACTCATGAA
      TATTTGGATT TGGCGCTAAT AGTGGAAATC ATCTTTTTGG AACAAGTTTG TTGAGTACTT
       L   G   L   G   R   N   D   G   K   T   S   F   G   Q   E   F   L   E   H   I

901   TTTTAGGGAT ATCATTACTA CATTTATTCA TAACGATAAA AGTGACAGAT TCCTCATTAT
      AAAATCCCTA TAGTAATGAT GTAAATAAGT ATTGCTATTT TCACTGTCTA AGGAGTAATA
       K   P   I   D   N   S   C   K   N   M   V   I   F   T   V   S   E   N   D

961   CGATGAATGC GATATTGATG AGTGGTTCCT CAAGATTTTC TGAAGCTTCA ATAGCATTAT
      GCTACTTACG CTATAACTAC TCACCAAGGA GTTCTAAAAG ACTTCGAAGT TATCGTAATA
       I   F   A   I   N   I   L   P   E   E   L   N   E   S   A   E   I   A   N   D

1021  CAACTATAAT ACCGATAATA CGACTAAGCT CAACAGTATT CATATCGATA CGATCAATTT
      GTTGATATTA TGGCTATTAT GCTGATTCGA GTTGTCATAA GTATAGCTAT GCTAGTTAAA
       V   I   I   G   I   I   R   S   L   E   V   T   N   M   D   I   R   D   I   E

1081  CATCAGGAAC CTCAATACTA ATTGGAATAC GTTTTCTTG  AGCTTGAATA ATTTTAGTAG
      GTAGTCCTTG GAGTTATGAT TAACCTTATG CAAAAGAAC  TCGAACTTAT TAAAATCATC
       D   P   V   E   I   S   I   P   I   R   K   E   Q   A   Q   I   I   K   T   T

1141  TAATCAGCCC TTTAATTTCT CTCACTTTCA ACTTTTCAAT ACCATTCATT TTAATAGAGC
      ATTAGTCGGG AAATTAAAGA GAGTGAAAGT TGAAAAGTTA TGGTAAGTAA AATTATCTCG
       I   L   G   K   I   E   R   V   K   L   K   E   I   G   N   M   K   I   S   R

1201  GAGTTTTTAA TTTATCTTTC ATTGGAACGA TATTTTCATT AAAATATTTA CGTAATCCAG
      CTCAAAAATT AAATAGAAAG TAACCTTGCT ATAAAAGTAA TTTTATAAAT GCATTAGGTC
       T   K   L   K   D   K   M   P   V   I   N   E   N   F   Y   K   R   L   G   P

1261  GCATATCATC TTCTCTAATG TAATCTGAAA GAGTGGTGAG GATATTCACA TAATCATGTC
      CGTATAGTAG AAGAGATTAC ATTAGACTTT CTCACCACTC CTATAAGTGT ATTAGTACAG
       M   D   D   E   R   I   Y   D   S   L   T   T   L   I   N   V   Y   D   H   R

1321  GGAACTTACG CATTTCATTG TTAATGCTTT CTATACGTAA CGTGTACTCA TAATATGCTT
      CCTTGAATGC GTAAAGTAAC AATTACGAAA GATATGCATT GCACATGAGT ATTATACGAA
       F   K   R   M   E   N   N   I   S   E   I   R   L   T   Y   E   Y   Y   A   E

1381  CGATTTCTTT TACATTACGT TTATACCTCA TTTCACGGAG TGTAAAATTG GACATCACTA
      GCTAAAGAAA ATGTAATGCA AATATGGAGT AAAGTGCCTC ACATTTTAAC CTGTAGTGAT
       I   E   K   V   N   R   K   Y   R   M   E   R   L   T   F   N   S   M   V   L

1441  ATATCACTAC ACTTAAAAAA ACCATAATAC CCAACAATAA GATGGCATAT AATTTAAGGG
      TATAGTGATG TGAATTTTTT TGGTATTATG GGTTGTTATT CTACCGTATA TTAAATTCCC
       I   V   V   S   L   F   V   M   I   G   L   L   L   I   A   Y   L   K   L   T

1501  TATCATTTCC TCGCATATCA GTTTGTGACA CCATATAAAG TAAAATAAAT GATATGAAAA
      ATAGTAAAGG AGCGTATAGT CAAACACTGT GGTATATTTC ATTTTATTTA CTATACTTTT
       D   N   G   R   M   D   T   Q   S   V   M   Y   L   L   I   F   S   I   F   L
```

FIG.1A-2

```
1561  GTACTATTGT TATTATCAAT AAGTATCTTT TATTGAGTGA CAAGTAGGAT ACTTTTAATT
      CATGATAACA ATAATAGTTA TTCATAGAAA ATAACTCACT GTTCATCCTA TGAAAATTAA
       V  I  T   I  I  L   Y  R  N   L  S  L   Y  S  V   K  L

1621  TATTGAACAA TAGTTGAGTT AAATAAGCAA TAATTAGAGT TATGATTACA AAAGAGGTAA
      ATAACTTGTT ATCAACTCAA TTTATTCGTT ATTAATCTCA ATACTAATGT TTTCTCCATT
       N  F  L   Q  T  L   Y  A  I   I  L  T   I  I  V   F  S  T  F

1681  AATGTATTAA CTGTAAAGCA AATTTAAACG GAATATAATC TTTTATAGTC AAATGTATGT
      TTACATAATT GACATTTCGT TTAAATTTGC CTTATATTAG AAAATATCAG TTTACATACA
       H  I  L   Q  L  A  F  K  F  P   I  Y  D   K  I  T   L  H  I  Y

1741  ATACAGTTAT GAAATTAGTT ATATATAAGA TCATAGTGGT GAATAATACA ACTAATATTG
      TATGTCAATA CTTTAATCAA TATATATTCT AGTATCACCA CTTATTATGT TGATTATAAC
       V  T  I   F  N  T   I  Y  L   I  M  T  T   F  L  V  V   L  I  S

1801  AATAAAGCTT TATTTTTGTA TAAAAGAAAA TGGTGATTAT TATAACCAAA ACTATTAATG
      TTATTTCGAA ATAAAAACAT ATTTTCTTTT ACCACTAATA ATATTGGTTT TGATAATTAC
       Y  L  K   I  K  T   Y  F  F  I   T  I  I   I  V  L   V  I  L  A

1861  CTTTACTTTG CCAAAAGTAA TACATTATTG CAGAAGGGAT TACAATCGTA AAAACGATTA
      GAAATGAAAC GGTTTTCATT ATGTAATAAC GTCTTCCCTA ATGTTAGCAT TTTTGCTAAT
       K  S  Q   W  F  Y   Y  M  I  A   S  P  I   V  I  T   F  V  I  I

1921  TGTAATCCCT AAAATTAAAT TTCATATTAA TGATAACTTT AGTAACCCAA ATCATTAAAA
      ACATTAGGGA TTTTAATTTA AAGTATAATT ACTATTGAAA TCATTGGGTT TAGTAATTTT
       Y  D  R   F  N  F   K  M  N  I   I  V  K   T  V  W   I  M  L  F

1981  AGATTTGTAG GCCTGCAAAC GGAAATAGAT TAATATCATC CATATCTTAC ACACTTTCTA
      TCTAAACATC CGGACGTTTG CCTTTATCTA ATTATAGTAG GTATAGAATG TGTGAAAGAT
       I  Q  L   G  A  F   P  F  L   N  I  D   D  M  agrC 2041  GGGTTATATT TACTCGTATA GTTTAGTCAG TTCTTCTGGT ACTTCTGGTT CGTCAAAGTA
      CCCAATATAA ATGAGCATAT CAAATCAGTC AAGAAGACCA TGAAGACCAA GCAGTTTCAT
              *   E  Y  L   K  T  L   E  E  P   V  E  P   E  D  F  Y 2101  AGAGGCACAT ACACTATCTC CTGCTACAGT ACCAATAAAT TCCAAGATTG TAGTGAAAAA
      TCTCCGTGTA TGTGATAGAG GACGATGTCA TGGTTATTTA AGGTTCTAAC ATCACTTTTT
       S  A  C   V  S  D   G  A  V   T  G  I   F  E  L   I  T  T  F  F 2161  TTTTATAAAT AAATTAAAAA TGATTTCCAT GATTAATATC CTCCTTAGGG AAAAAGATGG
      AAAATATTTA TTTAATTTTT ACTAAAGGTA CTAATTATAG GAGGAATCCC TTTTTCTACC
       K  I  F   L  N  F  I   I  E  M   agrD
                        *   F  H  N  G  H  N  I   D  E  K  P  F  I  P 2221  GTAGTAATGT TAAAGATTCT AAAATTACAC CGAATAAAAT AAGTTTATTT ACCGGTTCTT
      CATCATTACA ATTTCTAAGA TTTTAATGTG GCTTATTTTA TTCAAATAAA TGGCCAAGAA
       L  L  T   L  S  E  L   I  V  G   F  L  I   L  K  N   V  P  E  K 2281  TAGTTACTAA TGAAATAACT ACGATAGTAC AATATAAAAA TATGGAGAGT ATTTTTTTTC
      ATCAATGATT ACTTTATTGA TGCTATCATG TTATATTTTT ATACCTCTCA TAAAAAAAAG
       T  V  L   S  I  V  V   I  T  C   Y  L  F   I  S  L   I  K  K  R
```

FIG.1A-3

```
2341  GCTTTACAAG ACGTCTAGGT ATAGGTTGTT TCTTAGTTGC TGCAGGTGCG TATAAAATGG
      CGAAATGTTC TGCAGATCCA TATCCAACAA AGAATCAACG ACGTCCACGC ATATTTTACC
       K  V  L   R  R  P  I   P  Q  K   K  T  A    A  P  A   Y  L  I  T

2401  TAATAATTAA TCCGACTAAT GCCATAGATA AAAGAACAAA ATAGTTAATA TCTAACTTTA
      ATTATTAATT AGGCTGATTA CGGTATCTAT TTTCTTGTTT TATCAATTAT AGATTGAAAT
       I  I  L   G  V  L  A   M  S  L    L  V  F   Y  N  I   D  L  K  I

2461  TTATTAAGTA TGGAAAGATA ATAAAGAAAA TTATGTTCTG AATATGACAT AACAATGACG
      AATAATTCAT ACCTTTCTAT TATTTCTTTT AATACAAGAC TTATACTGTA TTGTTACTGC
       I  L  Y   P  F  I    I  F  F  I   I  N  Q   I  H  C   L  L  S  S

2521  AATTTGCATG CGTACCGTGT GCATGTCTCC TAATTAAAAA ATAACTTAAA TGAGTTAAAA
      TTAAACGTAC GCATGGCACA CGTACAGAGG ATTAATTTTT TATTGAATTT ACTCAATTTT
       N  A  H   T  G  H  A   H  R  R    I  L  F   Y  S  L   H  T  L  L

2581  GTGTGTAAAA GAAAGTATGA AAGATTATTG CTAGCCCATA CACAACTATA GACTTTTCAA
      CACACATTTT CTTTCATACT TTCTAATAAC GATCGGGTAT GTGTTGATAT CTGAAAAGTT
       T  Y  F   F  T  H  F   I  I  A    L  G  Y   V  V  I   S  K  E  I

2641  TATTTATCGC TAGTACCTGC ATCCCTAAAC GAATTTTTAG AAACTGTATG TGATCTAAGT
      ATAAATAGCG ATCATGGACG TAGGGATTTG CTTAAAAATC TTTGACATAC ACTAGATTCA
       N  I  A    L  V  Q  M   G  L  R   I  K  L    F  Q  I   H  D  L  N

2701  TATTTTTACG TACGTTGTAA ATATGAGCAA ATTGCTCAAT TTTTTTATCG ATGATTTCA
      ATAAAAATGC ATGCAACATT TATACTCGTT TAACGAGTTA AAAAAATAGC TACTAAAAGT
       N  K  R   V  N  Y  I   H  A  F    Q  E  I   K  K  D   I  K

2761  CTTGTTTACT ACTCTCCTCA AGTGTCATTA TACAATTTTG CGCAACATTT TTTAGAAAGC
      GAACAAATGA TGAGAGGAGT TCACAGTAAT ATGTTAAAAC GCGTTGTAAA AAATCTTTCG
       M  agrB 2821  ATGCCTAACT GTTAAAAAAA TATACCTAAG TGTTTTAATT AAGTACTATT AGATATTTTA
      TACGGATTGA CAATTTTTTT ATATGGATTC ACAAAATTAA TTCATGATAA TCTATAAAAT 2881  CCATATTTAG TTTTACAGTT GAGTACTAAA TATTGCTATT TACGAAATTT TAATCTTTAA
      GGTATAAATC AAAATGTCAA CTCATGATTT ATAACGATAA ATGCTTTAAA ATTAGAAATT 2941  ATGGAAAAAT CATGTTTTAA TAGACTCATA TCACAGTGAT GTGATTGAAA GATAGTTGAA
      TACCTTTTTA GTACAAAATT ATCTGAGTAT AGTGTCACTA CACTAACTTT CTATCAACTT 3001  AAATTTGCTT AATCTAGTCG AGTGAATGTT AAATTCATTC GTATCCATTA CCTTAATTCG
      TTTAAACGAA TTAGATCAGC TCACTTACAA TTTAAGTAAG CATAGGTAAT GGAATTAAGC hld  M   A  A  D  I   I  S  T    I  G  D   L  V  K
3061  AAAGGAGTGA AGTTATAATG GCAGCAGATA TCATTTCTAC AATCGGTGAT TTAGTAAAAT
      TTTCCTCACT TCAATATTAC CGTCGTCTAT AGTAAAGATG TTAGCCACTA AATCATTTTA W  I  D   T  V  N   K  F  K  K   *
3121  GGATTATCGA TACAGTTAAT AAATTCAAAA AATAATTTTT GAATGAGTCT ATTGTAACTT
      CCTAATAGCT ATGTCAATTA TTTAAGTTTT TTATTAAAAA CTTACTCAGA TAACATTGAA 3181  TTGTAACTTT GTTTTCTTCG TATAATTAAT ATTATTAGTG AGTTGTTGAG CCATCCCAAC
      AACATTGAAA CAAAAGAAGC ATATTAATTA TAATAATCAC TCAACAACTC GGTAGGGTTG
```

FIG.1A-4

```
3241  TTAATAATTT ACTAATATAA ACTAAGCAAG TGAGAAGCAT TTGCTAGTAG CTGTAGTTTC
      AATTATTAAA TGATTATATT TGATTCGTTC ACTCTTCGTA AACGATCATC GACATCAAAG

3301  CTTGGACTCA GTGTTACGTA TTATTCTTAG CTACCTTAAA TAGGTAATTA TTTCTAGCAT
      GAACCTGAGT CACAATGCAT AATAAGAATC GATGGAATTT ATCCATTAAT AAAGATCGTA

3361  GTAAGCTATC GTAAACAACA TTCAATTTAT CATGTTAAAT AGATAAATTC ACTAAAAATT
      CATTCGATAG CATTTGTTGT AAGTTAAATA GTACAATTTA TCTATTTAAG TGATTTTTAA

3421  TTTTCATAAT TAATAACATC CCCAAAAAAT AGATTGAAAA AATAACTGTA AAAACATTCC
      AAAAGTATTA ATTATTGTAG GGGTTTTTTA TCTAACTTTT TTATTGACAT TTTTGTAAGG

3481  CTTAATAATA AGTTATCAAG CCGTGAGTCT CTCCCAAGCT CACGGCTT
      GAATTATTAT TCAATAGTTC GGCACTCAGA GAGGGTTCGA GTGCCGAA
```

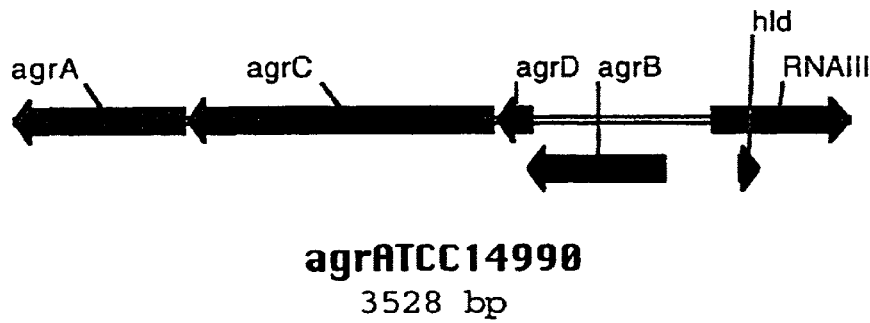

agrATCC14990
3528 bp

FIG.1A-5

```
  1  TTATATTTTT TTAACATTAC GTACTGAAGC GAAACAATTT TCGCCATTCT TAAAGTAAAC
     AATATAAAAA AATTGTAATG CATGACTTCG CTTTGTTAAA AGCGGTAAGA ATTTCATTTG
      *  I  K  K  V  N  R  V  S  A  F  C  N  E  G  N  K  F  Y  V

61  AATACGTTCT TTTGAGTCAA TAGATTCAAT ATTATGCCTG TTTATCACAA AACTGTTATG
     TTATGCAAGA AAACTCAGTT ATCTAAGTTA TAATACGGAC AAATAGTGTT TTGACAATAC
      I  R  E  K  S  D  I  S  E  I  N  H  R  N  I  V  F  S  N  H

121  ACATCTAAAG AAACGTTCAT CAAGCTGTGC TAATTCCTTT AAATTTCCAT AAAATTCAAT
     TGTAGATTTC TTTGCAAGTA GTTCGACACG ATTAAGGAAA TTTAAAGGTA TTTTAAGTTA
      C  R  F  F  R  E  D  L  Q  A  L  E  K  L  N  G  Y  F  E  I

181  TTGCCGATTA TCAAGATGTG CGATGAGTCT ATGAGATTTC GTAGATGATT CAAAAAACAT
     AACGGCTAAT AGTTCTACAC GCTACTCAGA TACTCTAAAG CATCTACTAA GTTTTTTGTA
      Q  R  N  D  L  H  A  I  L  R  H  S  K  T  S  S  E  F  F  M

241  AATATCATCA TATTGAACGT ATACTGAATT ACTTCCCCGC TTTAACTCAA TCGTATCTAC
     TTATAGTAGT ATAACTTGCA TATGACTTAA TGAAGGGGCG AAATTGAGTT AGCATAGATG
      I  D  D  Y  Q  V  Y  V  S  N  S  G  R  K  L  E  I  T  D  V

301  ATTACTTTCT TTTGATAATA ATTTGAGTCG TGTATGTGCT GTTTCAAGAC AATCTATGAT
     TAATGAAAGA AAACTATTAT TAAACTCAGC ACATACACGA CAAAGTTCTG TTAGATACTA
      N  S  E  K  S  L  L  K  L  R  T  H  A  T  E  L  C  D  I  I

361  TCTCATTTTT AATTCAGATG GATCATCCTT AAAAATAAAA TCCATAGCAG CCACTTTATA
     AGAGTAAAAA TTAAGTCTAC CTAGTAGGAA TTTTTATTTT AGGTATCGTC GGTGAAATAT
      R  M  K  L  E  S  P  D  D  K  F  I  F  D  M  A  A  V  K  Y

421  AACAAACGTC AAATAAGTCA GTTCACTGTG ACTGGTTACA AATATAATAT TACCAACAGG
     TTGTTTGCAG TTTATTCAGT CAAGTGACAC TGACCAATGT TTATATTATA ATGGTTGTCC
      V  F  T  L  Y  T  L  E  S  H  S  T  V  F  I  I  N  G  V  P

481  ATCATGTTTA CGAATTTCAC TGGCTAATTT AATACCGTTC ATATCAGCTT CTAATTGAAT
     TAGTACAAAT GCTTAAAGTG ACCGATTAAA TTATGGCAAG TATAGTCGAA GATTAACTTA
      D  H  K  R  I  E  S  A  L  K  I  G  N  M  D  A  E  L  Q  I

541  ATCAAGGAAG TAACAACCAA TGTCATTAAG TTCTTTTGAT TGCTCTAAGA CCTCATAAGG
     TAGTTCCTTC ATTGTTGGTT ACAGTAATTC AAGAAAACTA ACGAGATTCT GGAGTATTCC
      D  L  F  Y  C  G  I  D  N  L  E  K  S  Q  E  L  V  E  Y  P

601  ATCATTTGTT GCTAAGGCTA ACTCCATTGG CTTTTCTTCA ATCATTATGT AGTTTTTAAT
     TAGTAAACAA CGATTCCGAT TGAGGTAACC GAAAAGAAGT TAGTAATACA TCAAAAATTA
      D  N  T  A  L  A  L  E  M  P  K  E  E  I  M  I  Y  N  K  I

661  GATTGATACC ATATGTTCTC TTTGTCTTTG GTCATCTTCA CAAACAAAAA TTTTCATTTA
     CTAACTATGG TATACAAGAG AAACAGAAAC CAGTAGAAGT GTTTGTTTTT AAAAGTAAAT
      I  S  V  M  H  E  R  Q  R  Q  D  D  E  C  V  F  I  K  M agrA 721  ATTCTACACA TCCTTATGAT TCCTTATTAT TTATTTCTAC TTTTTGTACA AAGTAACCAT
     TAAGATGTGT AGGAATACTA AGGAATAATA AATAAAGATG AAAAACATGT TTCATTGGTA
                 *  S  E  K  N  N  I  E  V  K  Q  V  F  Y  G  N
```

FIG.1B-1

```
 781   TTTCGATGAC AGTATCTAAT AAAACATTCT CGTTTGAGTC TGTCAGTTCT TTTAAAGTTG
       AAAGCTACTG TCATAGATTA TTTTGTAAGA GCAAACTCAG ACAGTCAAGA AAATTTCAAC
         E   I   V    T   D   L    V   N   E    N   S   D    T   L   E   K   L   T   S

841   ATAAACCTAA ACCGCGATTA TCACCTTTAG TAGAAAAACC TTGTTCAAAC AACTCATGAA
       TATTTGGATT TGGCGCTAAT AGTGGAAATC ATCTTTTTGG AACAAGTTTG TTGAGTACTT
         L   G   L    G   R   N   D    G   K   T    S   F   G    Q   E   F   L   E   H   I

901   TTTTAGGGAT ATCATCACTA CATTTATTCA TAACGATAAA AGTGACAGAT TCCTCATTAT
       AAAATCCCTA TAGTAGTGAT GTAAATAAGT ATTGCTATTT TCACTGTCTA AGGAGTAATA
         K   P   I    D   D   S   C    K   N   M    V   I   F    T   V   S   E   N   D

961   CGATGAATGC GATATTGATG AGTGGTTCCT CAAGATTTTC TGAAGCTTCA ATTGCATTAT
       GCTACTTACG CTATAACTAC TCACCAAGGA GTTCTAAAAG ACTTCGAAGT TAACGTAATA
         I   F   A    I   N   I    L   P   E   E    L   N   E    S   A   E   I   A   N   D

1021   CAACTATAAT ACCGATAATA CGACTAAGCT CAACAGTATT CATATCGATA CGATCAATTT
       GTTGATATTA TGGCTATTAT GCTGATTCGA GTTGTCATAA GTATAGCTAT GCTAGTTAAA
         V   I   I    G   I   I   R    S   L   E    V   T   N    M   D   I   R   D   I   E

1081   CATCAGGAAC CTCAATACTA ATTGGAATAC GTTTTTCTTG AGCTTGAATA ATTTTAGTAG
       GTAGTCCTTG GAGTTATGAT TAACCTTATG CAAAAAGAAC TCGAACTTAT TAAAATCATC
         D   P   V    E   I   S   I    P   I   R    K   E   Q    A   Q   I   I   K   T   T

1141   TAATCAACCC TTTAATTTCT CTCACTTTCA ACTTTTCAAT ACCATTCATT TTAATAGAGC
       ATTAGTTGGG AAATTAAAGA GAGTGAAAGT TGAAAAGTTA TGGTAAGTAA AATTATCTCG
         I   L   G    K   I   E   R    V   K   L    K   E   I    G   N   M   K   I   S   R

1201   GAGTTTTTAA TTTATCTTTC ATTGGAACGA TATTTCATT AAAATATTTA CGTAATCCAG
       CTCAAAAATT AAATAGAAAG TAACCTTGCT ATAAAGTAA TTTTATAAAT GCATTAGGTC
         T   K   L    K   D   K   M    P   V   I    N   E   N    F   Y   K   R   L   G   P

1261   GCATATCATC TTCTCTTATG TAATCTGAAA GAGTGGTGAG GATATTCACA ATAATCATGCC
       CGTATAGTAG AAGAGAATAC ATTAGACTTT CTCACCACTC CTATAAGTGT ATTAGTACGG
         M   D   D    E   R   I   Y    D   S   L    T   T   L    I   N   V   Y   D   H   R

1321   GGAACTTACG CATTTCATTG TTAATGCTTT CTATACGTAA CGTGTATTCA TAATATGCTT
       CCTTGAATGC GTAAAGTAAC AATTACGAAA GATATGCATT GCACATAAGT ATTATACGAA
         F   K   R    M   E   N   N    I   S   E    I   R   L    T   Y   E   Y   A   E

1381   CGATTTCTTT TACATTACGT TTATACCTCA TTTCACGAAG TGTAAAATTG GACATCACTA
       GCTAAAGAAA ATGTAATGCA AATATGGAGT AAAGTGCTTC ACATTTTAAC CTGTAGTGAT
         I   E   K    V   N   R   K    Y   R   M    E   R   L    T   F   N   S   M   V   L

1441   AAATCACTAC ACTTAAAAAA ACCATAATAC CCATCAACAA GATGGCATAT AATTTAAGTG
       TTTAGTGATG TGAATTTTTT TGGTATTATG GGTAGTTGTT CTACCGTATA TTAAATTCAC
         I   V   V    S   L   F   V    M   I   G    M   L   L    I   A   Y   L   K   L   T

1501   TATCATTTCC TCGCATATCA GTTTGTGACA CCATATAAAG TAAAATAAAT GATATAAAAA
       ATAGTAAAGG AGCGTATAGT CAAACACTGT GGTATATTTC ATTTTATTTA CTATATTTTT
         D   N   G    R   M   D   T    Q   S   V    M   Y   L    L   I   F   S   I   F   L
```

FIG.1B-2

```
1561  GTACAATTGT TATTATGAAT AAGTATCTTT TATTGAGTGA CAAATAGGAT ACTTTTAATT
      CATGTTAACA ATAATACTTA TTCATAGAAA ATAACTCACT GTTTATCCTA TGAAAATTAA
       V  I  T   I  I  F  L  Y  R   N  L  S   L  Y  S   V  K  L  K

1621  TATTGAACAA TAGTTGAGTT AAATAAGCAA TGATTAGAGT TATGATTACA AAAAAGGTAA
      ATAACTTGTT ATCAACTCAA TTTATTCGTT ACTAATCTCA ATACTAATGT TTTTTCCATT
       N  F  L   L  Q  T   L  Y  A  I   I  L  T    I  I  V    F  T  F

1681  AATGTATTAA CTGTAAAACA AATTTAAACG GAATATAATC TTTTATAGTT AAATGTATGT
      TTACATAATT GACATTTTGT TTAAATTTGC CTTATATTAG AAAATATCAA TTTACATACA
       H  I  L   Q  L  V   F  K  F   P  I  Y  D   K  I  T   L  H  I  Y

1741  ATACAGTTAT GAAATTAGTT ATATATAAGA TCATAGTCGT GAATAATACA ACTAATATTG
      TATGTCAATA CTTTAATCAA TATATATTCT AGTATCAGCA CTTATTATGT TGATTATAAC
       V  T  I   F  N  T  I   Y  L  I    M  T  T     F  L  V  V    L  I  S

1801  AATAAAGTTT TATTTTTGTA TAAAAGAAAA TGATGATTAT TATAACCAAA ACTATTAATG
      TTATTTCAAA ATAAAAACAT ATTTTCTTTT ACTACTAATA ATATTGGTTT TGATAATTAC
       Y  L  K    I  K  T  Y    F  F  I    I  I  I    V  L  V    I  L  A

1861  CTTTACTTTG CCAAAAGTAA TACATTATAG CAGAAGGGAT TACAATCGTA AAAACGATTA
      GAAATGAAAC GGTTTTCATT ATGTAATATC GTCTTCCCTA ATGTTAGCAT TTTTGCTAAT
       K  S  Q   W  F  Y  Y    M  I  A    S  P  I    V  I  T    F  V  I  I

1921  TGTAATCCCT AAAATTAAAT TCATATTAA TGATAACTTT AGTAACCCAA ATCATTAAAA
      ACATTAGGGA TTTTAATTTA AGTATAATT ACTATTGAAA TCATTGGGTT TAGTAATTTT
       Y  D  R    F  N  F  K    M  N  I    I  V  K    T  V  W    I  M  L  F

1981  AGATTTGTAG GCCTGCAAAC GGAAATAAAT TAATATCATC CATATCTTAC ACACTTTCTA
      TCTAAACATC CGGACGTTTG CCTTTATTTA ATTATAGTAG GTATAGAATG TGTGAAAGAT
       I  Q  L   G  A  F  P    F  L  N    I  D  D    M agrC 2041  GGGTTATATT TACTCGTATA GTTTAGTCAG TTCTTCTGGC ACTTCTGGTT CGTCAAAGTA
      CCCAATATAA ATGAGCATAT CAAATCAGTC AAGAAGACCG TGAAGACCAA GCAGTTTCAT
          *    E  Y  L    K  T  L    E  E  P    V  E  P    E  D  F  Y 2101  AGAAGCACAT ACACTATCTC CTGCTACAGT ACCAATAAAT TCCAAGATTG TAGTGAAAAA
      TCTTCGTGTA TGTGATAGAG GACGATGTCA TGGTTATTTA AGGTTCTAAC ATCACTTTTT
       S  A  C   V  S  D  G    A  V  T    G  I  F  E    L  I  T    T  F  F 2161  TTTTATAAAT AAATTAAAAA TGTTTTCCAT GATTAATATC CTCCTTAGGG AAAAGATGG
      AAAATATTTA TTTAATTTTT ACAAAAGGTA CTAATTATAG GAGGAATCCC TTTTTCTACC
                  *   F    H  K  G  H    N  I  D    E  K  P    F  F  I  P
       K  I  F  L    N  F  I    N  E  M agrD 2221  GTAGTAATGT TAAAGATTCT AAAATTACAC CGAATAAAAT AAGTTTATTT ACCGGTTCTT
      CATCATTACA ATTTCTAAGA TTTTAATGTG GCTTATTTTA TTCAAATAAA TGGCCAAGAA
       L  L  T   L  S  E  L    I  V  G    F  L  I    L  K  N    V  P  E  K 2281  TAGTTAATAA TGAAATAACT ACGATAGTAC AATATAAAAA TATGGAGAGT ATTTTTTTTC
      ATCAATTATT ACTTTATTGA TGCTATCATG TTATATTTTT ATACCTCTCA TAAAAAAAAG
       T  L  L   S  I  V  V    I  T  C    Y  L  F    I  S  L  I    K  K  R
```

FIG.1B-3

```
2341  GCTTTACAAG ACGTCTAGGT ATAGGTTGTT TCTTAGTTGC TGCAGGTGCG TATAAAATGG
      CGAAATGTTC TGCAGATCCA TATCCAACAA AGAATCAACG ACGTCCACGC ATATTTACC
        K   V   L    R   R   P    I   P   Q   K    T   A    A   P   A   Y    L   I   T

2401  TAATAATTAA TCCGACTAAT GCCACAGATA AAAGAACAAA ATAGTTAATA TCTAACTTTA
      ATTATTAATT AGGCTGATTA CGGTGTCTAT TTTCTTGTTT TATCAATTAT AGATTGAAAT
        I   I   L    G   V   L   A    V   S   L    L   V   F    Y   N   I   D    L   K   I

2461  TTATTAAGTA TGGAAAAATA ATAAAGAAAA TTATGTTCTG AATATGACAT AACAATGACG
      AATAATTCAT ACCTTTTTAT TATTTCTTTT AATACAAGAC TTATACTGTA TTGTTACTGC
        I   L   Y    P   F   I    F   F   I    N   Q    I   H   C    L   L   S    S

2521  AATTTGCATG TGTACCGTGT GCATGTCTCC TAATTAAAAA ATAACTTAAA TGAGTTAAAA
      TTAAACGTAC ACATGGCACA CGTACAGAGG ATTAATTTTT TATTGAATTT ACTCAATTTT
        N   A   H    T   G   H    A   H   R   R    I   L   F    Y   S   L    H   T   L   L

2581  GTGTGTAAAA GAAAGTATGA AAGATTATTG CTAGCCCATA CACAACTATA GACTTTTCAA
      CACACATTTT CTTTCATACT TTCTAATAAC GATCGGGTAT GTGTTGATAT CTGAAAAGTT
        T   Y   F    F   T   H   F    I   I   A    L   G   Y    V   V   I   S    K   E   I

2641  TATTTATTGC TAGTACCTGC ATTCCTAGAC GAATTTTCAA AAACTGTATG TGATCTAAGT
      ATAAATAACG ATCATGGACG TAAGGATCTG CTTAAAAGTT TTTGACATAC ACTAGATTCA
        N   I   A    L   V   Q    M   G   L    R   I   K   L    F   Q   I    H   D   L   N

2701  TATTTTTACG TTGTAAATAT TGAGCAAATT GCTCAATTTT TTTATCGATG ATTTCACTT
      ATAAAAATGC AACATTTATA ACTCGTTTAA CGAGTTAAAA AAATAGCTAC TAAAAGTGAA
        N   K   R    Q   L   Y    Q   A   F    Q   E   I   K    K   D   I   I    K  M agrB 2761  GTTACTACTC TCCTCAGGTG TCATTATACA ATTTTGCGCA ACATTTTTA GAAAGCATGC
      CAATGATGAG AGGAGTCCAC AGTAATATGT TAAAACGCGT TGTAAAAAAT CTTTCGTACG 2821  CTAACTGTTA AAAAAATATA CCTAAGTGTT TTAATTAAGT GCTATTAGAT ATTTTACCAT
      GATTGACAAT TTTTTTATAT GGATTCACAA AATTAATTCA CGATAATCTA TAAAATGGTA 2881  ATTTAGTTTT ACAGTTGAGT ACTAAATATT GCTATTTACG AAATTTTAAT CTTTAAATGG
      TAAATCAAAA TGTCAACTCA TGATTTATAA CGATAAATGC TTTAAAATTA GAAATTTACC 2941  AAAAATCATG TTTTAATAGA CTCATATCAC AGAGATGTGA TTGAAAGATA GTTGAAAAAT
      TTTTTAGTAC AAAATTATCT GAGTATAGTG TCTCTACACT AACTTTCTAT CAACTTTTA 3001  TTGCTTAATC TAGTCGAGTG AATGTTAAAT TCATTCGTAT CCATTACCTT AATTCGAAAG
      AACGAATTAG ATCAGCTCAC TTACAATTTA AGTAAGCATA GGTAATGGAA TTAAGCTTTC hld M   A   A   D   I   I    S   T   I    G   D   L    V   K   W   I
3061  GAGTGAAGTT ATAATGGCAG CAGATATCAT TTCTACAATC GGTGATTTAG TAAAATGGAT
      CTCACTTCAA TATTACCGTC GTCTATAGTA AAGATGTTAG CCACTAAATC ATTTTACCTA I   D   T    V   N   K   F    K   K   *
3121  TATCGATACA GTTAATAAAT TCAAAAAATA ATTTTTGAAT GAGTTTATTG TAACTTTTGT
      ATAGCTATGT CAATTATTTA AGTTTTTTAT TAAAAACTTA CTCAAATAAC ATTGAAAACA 3181  AACTTTGTTT TCTTCGTATA ATTAATACTA TTAGTGAGTT GTTGAGCCAT CCCAACTTAA
      TTGAAACAAA AGAAGCATAT TAATTATGAT AATCACTCAA CAACTCGGTA GGGTTGAATT
```

FIG.1B-4

```
3241  TAATTTACTA ATATAAACTA AGCAAGTGAG AAGCATTTGC TAGTAGCTGT AGTTTCCTTG
      ATTAAATGAT TATATTTGAT TCGTTCACTC TTCGTAAACG ATCATCGACA TCAAAGGAAC

3301  GACTCAGTGT TACGTATTAT TCTTAGCTAC CTTAAATAGG TAATTATTTC TAGCATGTAA
      CTGAGTCACA ATGCATAATA AGAATCGATG GAATTTATCC ATTAATAAAG ATCGTACATT

3361  GCTATCGTAA ACAACATTCA ATTTATCATG TTAAATAGAT AAATTCACTA AAATTTTTC
      CGATAGCATT TGTTGTAAGT TAAATAGTAC AATTTATCTA TTTAAGTGAT TTTAAAAAAG

3421  ATAATTAATA ACATCCCCAA AAAATAGATT GAAAAAATAA CTGTAAAAAC ATTCCCTTAA
      TATTAATTAT TGTAGGGGTT TTTTATCTAA CTTTTTTATT GACATTTTG TAAGGGAATT

3481  TAATAAGTTA TCAAGCCGTG AGTCTCTCCC AAGCTCACGG CTT
      ATTATTCAAT AGTTCGGCAC TCAGAGAGGG TTCGAGTGCC GAA
```

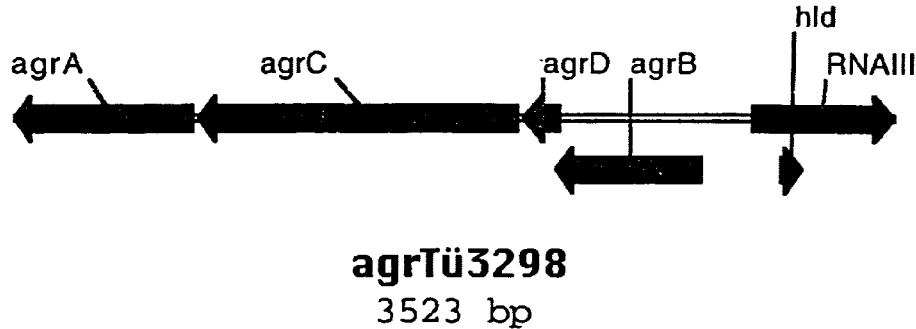

agrTü3298
3523 bp

FIG.1B-5

(BamHI)

TCCTCAAGTGTCATTATACAATTTTGCGCAACATTTTTTAGAAAGCATGCCTAACTGTTAAAAAATATACCTAAGTGTTTT
                                                      -35

AATTAAGTACTATTAGATATTTTACCATATATTTAGTTTTTACAGTTGAGTACTAAATATATTGCTATTTACGAAATTTTAATCTTT
              P3  -10     +1    BamHI

AAATGGAAAAAATCATGTTTAATAGACTCATATCACAGGATCCCGGGTACCGAGCTCGAATTCCGAGCTTGGATTTAAAATT
          Cat  M T F N I I K L E N

SD
AGGAGGAATTTATATATGACTTTTAAATATTATCAAATTAGAAAAT

LEAD SUBSTANCES AND THEIR USE AS THERAPEUTICS

The invention relates to peptides and their use in treatment of diseases caused by Staphylococci.

Staphylococci are amongst the most important pathogens of nosocomial infections. Nosocomial infections are often communicated by banal germs and take place simultaneously with medical care and nursing. They are often due to deficiencies in hygiene, lack of room in hospital and uncritical use of antibiotics. As a result of relative fast development of antibiotic resistance the conventional treatment of Staphylococcus infections by application of antibiotics is often without success and the spreading of pathogens is hardly to stop. That is why it is necessary to find new ways to treat such kind of infections.

The genus Staphylococcus comprises several species relevant[0ax4]o medicine, such as *S. aureus* and *S. epidermidis*, which are cause of various symptoms. These pathogens excrete toxins, enzymes or polysaccharides being crucial for the clinical picture. Many of these virulence factors are controlled by the so-called agr system (acessory gene regulator system) of the germs.

The invention has the object to provide new possibilities for treating diseases or disorders caused by Staphylococci, in particular by providing compounds, which are able to interfere with the regulation of the agr system in order to block the formation of different virulence factors.

This problem is solved by the peptides according the present invention. The nucleic acid sequence encoding for the peptides and the nucleic acid sequence of the agr system of Staphylococcus epidermidis and vectors comprising parts of said sequences are claimed herein. Appropriate hosts for the inventive vectors are shown herein. Pharmaceutical compositions and the use of the inventive chemical compounds in treating diseases and disorders are shown herein. The wording of all claims is hereby made to the content of the specification by reference.

As mentioned above many virulence factors, e.g. exoproteins, of Staphylococcus species, including alpha-toxin, beta-toxin, delta-toxin, serin protease, DNase, fibrinolysin, enterotoxin B, and toxic shock syndrome toxin-1, are controlled by the agr system. This is especially known for *S. aureus* (Novick et al., 1993).

The agr locus of *S. aureus*, about 3.5 kb in size, comprises the agrA, agrC, agrD, and agrB genes, which are cotranscribed (forming the mRNA RNAII), and the gene for a regulatory RNA molecule, RNAIII; the RNAIII DNA region also encodes the gene for the delta-toxin (hld). RNAIII controls the expression of target genes by an unknown mechanism. The agr genes are transcribed from the P2 promoter, and the RNAIII molecule is synthesized from the P3 promoter (Novick et al., 1995). The roles of AgrB and AgrD have recently become more clear. A small peptide is excised from the AgrD protein, modified, and secreted as the agr pheromone peptide into the surrounding medium. This peptide represents the autoinductive signal of the agr system; the pheromone activates the AgrC/AgrA two-component regulatory system that in turn activates transcription of the agrBDCA and RNAIII genes (Ji et al., 1997; Ji et al., 1995).

The peptides according to the invention e.g. block the action of the pheromone of *S. aureus* and therefore prevent the forming of virulence factors.

In the following the development and analysis of blocking chemical compounds is shown, also by reference to the figures and tables.

BRIEF DESCRIPTION OF THE DRAWINGS

FIGS. 1A & 1B DNA sequences of the *S. epidermidis* ATCC 14990 (SEQ ID Nos: 1–8) (A) and Tü3298 (SEQ ID Nos: 9–16) (B) agr systems. The shown sequences comprise the genes encoding the response regulator protein AgrA, the histidine kinase AgrC, the prepheromone protein AgrD, the putative pheromone maturation enzyme AgrB, and the gene for the regulatory RNAIII, which also encodes the gene for the, delta-toxin (hld). The RNAIII encoding region is underlined.

FIG. 3: P2/P3-promoter region of *S. epidermidis* ATCC 14990 cloned into pRB594. The figure shows the BamHI fragment obtained by PCR amplification comprising the P2/P3-promoter region of *S. epidermidis* ATCC 14990 which was cloned into the promoter test plasmid pRB594. Nucleotides shown in bold letters are identical to the *S. aureus* sequence (Peng et al., 1988). The −35 and −10 regions of the P3 promoter, and the transcription start site of RNAIII were deduced from the homology to the *S. aureus* sequence. The Shine-Dalgarno (SD)-sequence and the translation start with the N-terminal sequence of the CAT reporter enzyme are marked (SEQ ID Nos: 20–21.)

FIG. 5: Concentration-dependent suppression of delta-toxin production in *S. aureus* Newman by the addition of synthetic *S. epidermidis* pheromone or one of its derivatives. Media were inoculated with a 1/100 volume of an overnight preculture of *S. aureus* Newman. At the same time, the *S. epidermidis* pheromone or one of its derivatives was added at the given concentration. The peptides were dissolved in DMSO; the control received only DMSO. After 8 h of growth, the amount of produced delta-toxin was determined. The optical density (578 nm) at the harvest time was 2.9 for all cultures. (1) Synthetic *S. epidermidis* pheromone, DSVc [CASYF] (SEQ ID NO: 19), (2) thiolactone-containing GDSVc[CASYF] (SEQ ID NO: 17), (3) thiolactone-containing SVc[CASYF] (SEQ ID NO: 18), (4) lactam-containing octapeptide DSVc[XASYF] (SEQ ID NO: 19), (5) lactone-containing octapeptide DSVc[SASYF] (SEQ ID NO: 19).

TABLE 1

Figure 2B:
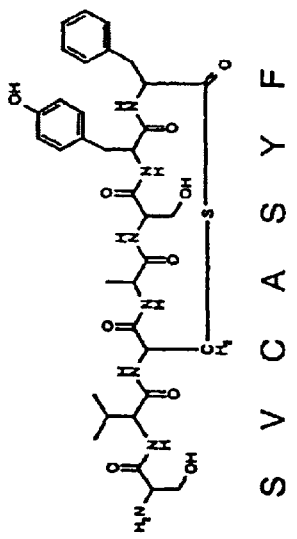
FIGS 2A, 2B & 2C: Structures of the compounds particularly those used in this study. a) Thiolactone-containing *S. epidermidis* pheromone harboring an additional glycine at the N-terminus (SEQ ID No: 17); b) thiolactone-containing *S. epidermidis* pheromone lacking the original aspartate residue at the N-terminus (compound 3)(SEQ ID No: 18) c) *S. epidermidis* pheromone with the original thiolactone structure (-S-); replaced by a lactone (-O-), a lactam (-NH-) or a keto (-$CH_2$-) structure. The keto (-$CH_2$-) structure can be provided by chemical reduction. Further the carbonyl (C=O) -group of the aforementioned thiolactone, lactone and lactam structures can be replaced by a methylen ($CH_2$) - group (SEQ ID No: 19).

Structures of chemically synthesized compounds.

| | | |
|---|---|---|
| a) Unmodified octapeptide: | (SEQ ID NO: 19) | DSVCASYF |
| b) Thiolactone-containing octapeptide: S. epidermidis pheromone containing an intramolecular thioester between the central cysteine and the C-terminal carboxy group (thiolactone) ("c" standing for "cyclic") | (SEQ ID NO: 19) | DSVc [CASYF] |
| c) Thiolactone-containing nonapeptide: S. epidermidis | (SEQ ID NO: 17) | GDSVc [CASYF] |

TABLE 1-continued

Structures of chemically synthesized compounds.

| | | |
|---|---|---|
| pheromone harboring an additional glycine at the N-terminus | | |
| d) Thiolactone-containing heptapeptide: S. epidermidis pheromone lacking the original aspartate residue at the N-terminus | (SEQ ID NO: 18) | SVc [CASYF] |
| e) Lactone-containing octapeptide: S. epidermidis pheromone in which the original thiolactone structure is replaced by a lactone structure by substitution of cysteine by serine (—O— compound) | (SEQ ID NO: 19) | DSVc [SASYF] |
| f) Lactam-containing octapeptide: S. epidermidis pheromone in which the original thiolactone structure is replaced by a lactam structure by substitution of cysteine by 1,3-diaminopropionic acid, (—NH—compound) | (SEQ ID NO: 19) | DSVc [XASYF] |
| g) Unmodified octapeptides: X, represents anyone of the biogenic amino acids | (SEQ ID NO: 19) | DSVXASYF |

TABLE 2

Inducing activities of the modified (thiolactone-containing) and unmodified peptides at a concentration of 200 nM in S. epidermidis.

| Peptide (200 nM) | Specific CAT activity (U/mg protein) |
|---|---|
| without peptide | 12.5 |
| GDSVCASYF (SEQ ID NO: 17) | 11.2 |
| GDSVCASYF modified | 15.6 |
| DSVCASYF (SEQ ID NO: 19) | 9.8 |
| DSVCASYF modified | 53.3 |
| SVCASYF (SEQ ID NO: 18) | 8.9 |
| SVCASYF modified | 16.1 |

TABLE 3

Delta-toxin production in S. aureus strains. The amount of delta-toxin detected in 1 ml of a 16 h culture grown in TSB is indicated.

| Strain | delta-toxin (µg) |
|---|---|
| RN 4220 (control) | 0 |
| 60/055 | 4.2 |
| Newman | 5.3 |
| 8325-4 | 4.4 |
| ATCC 33591 | 4.3 |
| ATCC 12600 | 0 |
| 6538 | 0 |
| SA113 | 0 |
| 502A | 0 | a) Culture filtrate (500 µl) of cells grown in basic medium for 16 h was injected onto a Resource PHE 1 ml column (Amersham Pharmacia Biotech, Freiburg, Germany). Peptides were eluted with a linear gradient from 0.1% TFA (trifluoroacetic acid) in water to 0.1% TFA in acetonitrile over 15 column volumes at a flow rate of 2 ml/min. The peaks at 280 nm were integrated, and the amount of delta-toxin was calculated by comparison to a known amount of synthetic delta-toxin.

1. sequence analysis of the S. epidermidis agr system

In order to understand the mechanism of the agr system and to [de]velop blocking reagents, first of all the agr system of S. epidermidis was analysed in detail.

The sequence of the S. epidermidis agr system was determined by primer walking. The first oligonucleotide that was used for sequencing was based on the DNA sequence of the 5' end of the coding region for the delta-toxin in S. aureus and the N-terminal amino acid sequence of the delta-toxin of S. epidermidis Tü3298. The entire coding region of the agr system was sequenced in S. epidermidis strains ATCC 14990 and Tü3298 (FIGS. 1A and 1B). The DNA sequence of the two strains was very similar. The coding region of only the peptide pheromone was sequenced in 15 S. epidermidis strains (strains ATCC 14990, Tü3298, 0–47 and 12 strains of hospital origin). The corresponding amino acid sequence was the same in all strains sequenced.

The hld region was sequenced in two additional S. epidermidis strains (0–47, RP62A). The delta-toxin amino acid sequence of RP62A was the same as that of S. epidermidis ATCC 14990 and Tü3298. The hld sequence of S. epidermidis 0–47 revealed an additional methionine codon directly upstream of the coding region, which was the consequence of a transition point mutation at position −1 from A to G.

Based on the Staphylococcus epidermidis ATCC 14990 and Staphylococcus epidermidis Tü3298 agrD DNA sequence an octapeptide with the protein sequence DSV-CASYF (SEQ ID NO: 19) was designed. This sequence is identical in 15 different S. epidermidis strains and it was therefore anticipated that it has a biological function (for DNA sequence analysis see Experimental procedures).

It was speculated that this peptide is post-translationally modified by AgrB (Ji et al., 1997; Ji et al., 1995). However, the mode of modification was not proven.

2. Chemical Synthesis of Modified and Unmodified Peptides

Figure 2A:
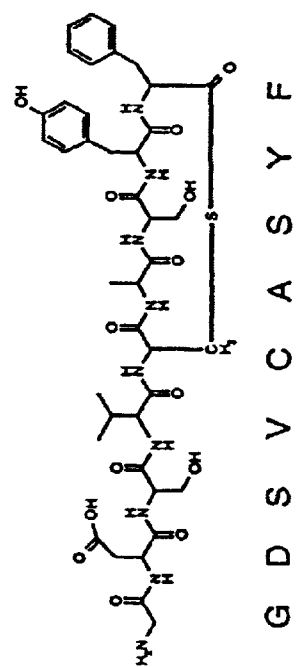
Figure 2C:
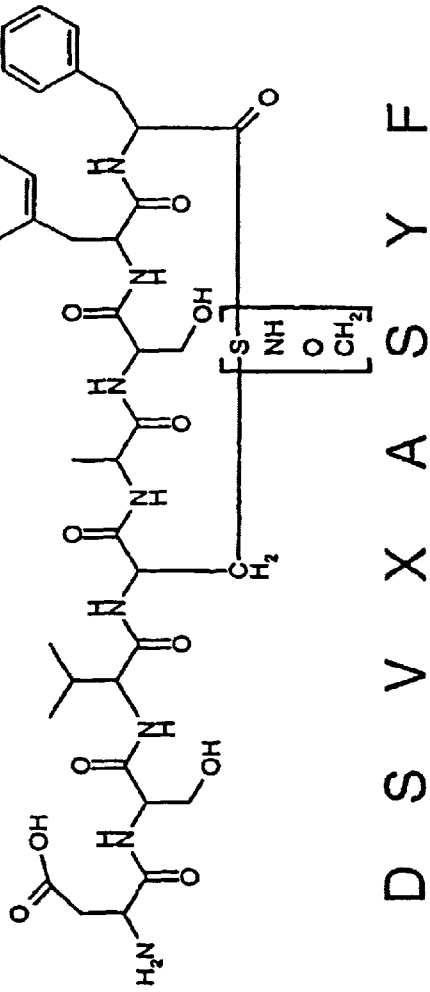

A number of modified and unmodified peptides derived from the core sequence DSVXASYF (SEQ ID NO: 19) (see Table 1 and FIG. 2) was chemically synthesized. The modification resulted in an intramolecular cyclic bond between the central cysteine, serine, or 1,3-diaminopropionic acid and the C-terminal carboxy group, thus the cyclic structure was based on either a thiolactone, lactone or lactam ring (for Synthesis of peptides see Experimental procedures). Additionally, thiolactone-containing peptides differing according to the peptidyl moiety expanding from the cyclic structure towards the N-terminus were synthesized, GDSVc[CASYF] (SEQ ID NO: 17), DSVc[CASYF] (SEQ ID NO: 19), and SVc[CASYF] (SEQ ID NO: 18) The -additional glycine residue is based on the AgrD prepheromone sequence. These compounds were also synthesized in order to investigate whether a correct cleavage of the AgrD prepheromone by the modification enzyme, presumably AgrB, is important for the production of a biologically active pheromone.

3. Biological Activities of the Compounds 3.1 Stimulating' Effect on P3 Promoter Activity in Staphylococcus epidermidis Using CM as a Reporter Enzyme In order to assay the biological activity of the synthetic peptides, an assay was developed that uses chloramphenicol acetyltransferase (CAT) as a reporter enzyme. The cat gene was clones under the control of the S. epidermidis agr P3 promoter region (FIG. 3). The resulting promoter test plasmid pRB594P3 harbors an erythromycin resistance gene. It was transformed in the erythromycin-sensitive S. epidermidis Tü3298 (for plasmid construction see Experimental procedures).

Figure 4:
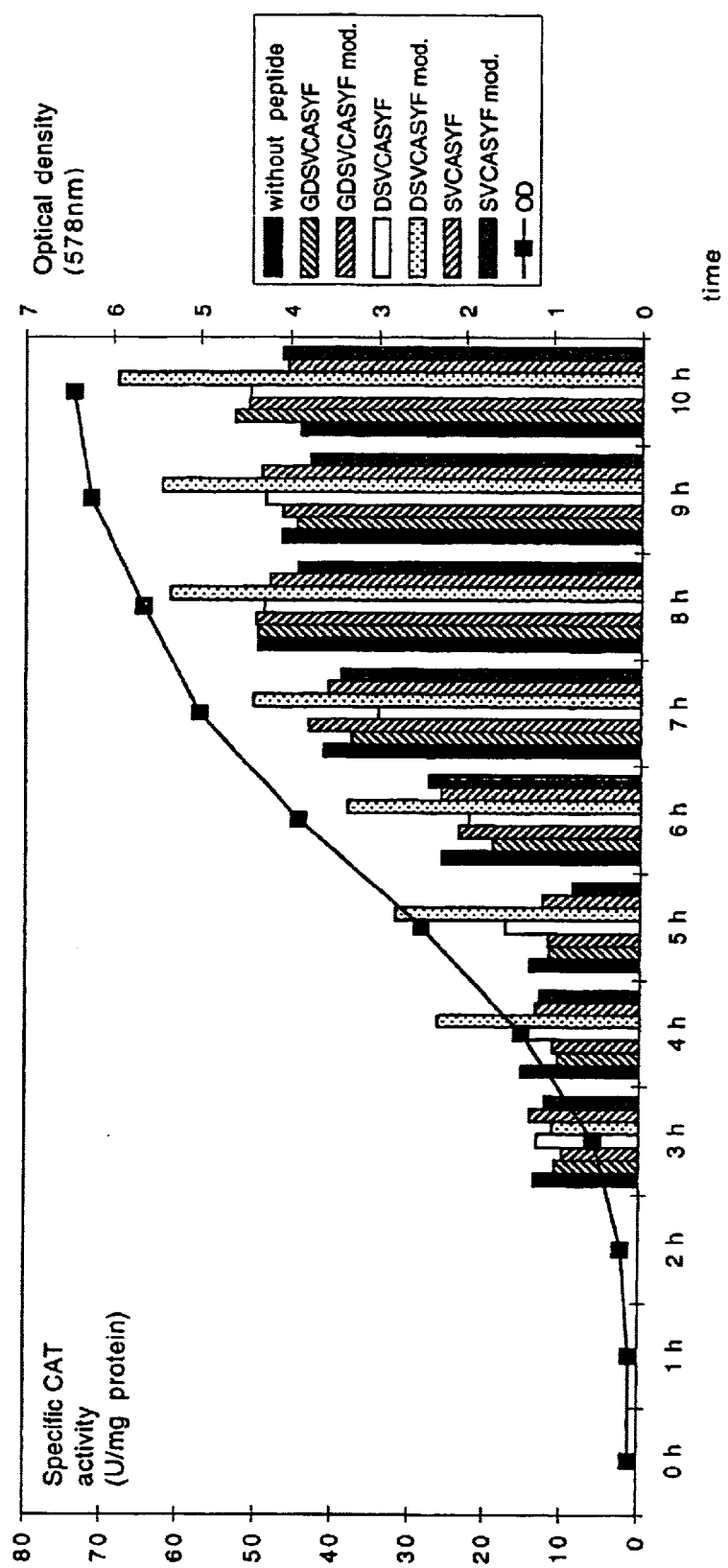
FIG. 4: CAT (Chloramphenicol acetyltransferase) expression in *S. epidermidis* Tü3298 (pRB594P3) upon addition of various synthesized peptides. Flasks containing 100 ml basic medium were inoculated with 1/100 vol. of an *S. epidermidis* Tü3298 (pRB594P3) preculture and grown with aeration for 10 h. The plasmid pRB594P3 harbours the cat reporter gene under the control of the agr P3 promoter. Optical densities of the cultures were determined hourly. Growth curves of all cultures were comparable. After 3 h of growth, the peptides SVCASYF, DSVCASYF, GDSVCASYF, as well as their thiolactone-containing modified counterparts ("mod."), were added to a final concentration of 20 nM. From this time on, cell extracts were prepared from samples taken every hour. Specific CAT activities were calculated from CAT activities and protein content determined in triplicate in every cell extract. Black bars show the CAT activities in the control to which no peptide was added, where CAT activity is effected only by the host-encoded agr system.

By measurement of CAT activity at different times during the growth of S. epidermidis Tü3298 (pRB594P3), it was demonstrated that the activity of the agr system in S. epidermidis Tü3298 is growth phase-dependent. At the end of exponential growth phase the CAT activity increased rapidly to a level that was maintained during stationary phase (FIG. 4—black bars).

When added to the test strain cultures of S. epidermidis Tü3298 (pRB594P3), the correct synthetic pheromone should increase CAT expression by its action on the host-encoded AgrA/AgrC two-component regulatory system, which regulates transcription from the P3 promoter. Because the host-encoded agr peptide pheromone was assumed to superimpose the exogenous activity during stationary phase, the synthetic peptides were added 3 h after inoculation when the background CAT activity was still low. All synthesized modified and unmodified peptides were applied at a concentration of 20 nM in this experiment. None of the unmodified peptides, the modified hepta-, or the modified nonapeptide, increased CAT activity when compared to the control. A significant increase of CAT activity (twofold after one hour of growth) was only found when the thiolactone containing octapeptide DSVc[CASYF] (SEQ ID NO: 19) was added (FIG. 4). This strongly suggests that this peptide is identical to the naturally occurring inducing agent, i.e. the natural agr peptide pheromone in S. epidermidis.

The relative inducing effect of the modified DSVc[CASYF] (SEQ ID NO: 19) peptide was highest at 1 h and 2 h after addition, and decreased afterwards, probably due to the onset of host-encoded pheromone expression. In the sample containing the modified DSVc[CASYF] (SEQ ID NO: 19) peptide, CAT activity was still somewhat higher in stationary phase compared to the controls (approximately 20%), which implies that the activity of the peptide added early in growth phase is still present after several hours.

The concentration-dependent effect of the modified octapeptide DSVc[CASYF] (SEQ ID NO: 19) on CAT expression was determined using concentrations between 5 and 500 nM. CAT activities were determined 2 h after addition of the peptide. A concentration of 10 nM was sufficient to result in a detectable increase in CAT activity, whereas concentrations higher than 100 nM could only slightly further increase the effect (for Chloramphenicol acetyltransferase (CAT) assay see Experimental procedures).

Figure 5:
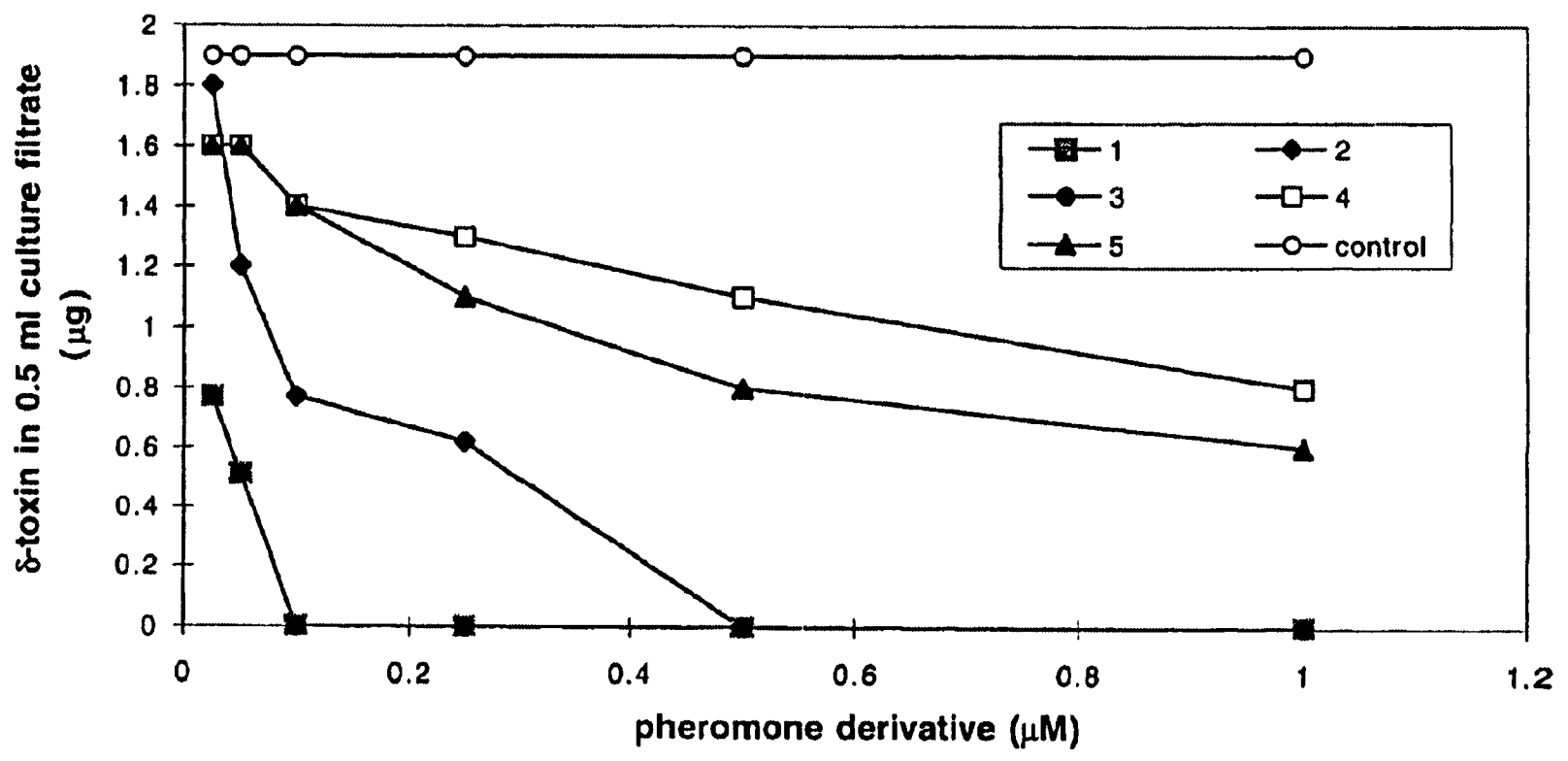

Even at a concentration of 200 nM, which is 10 times the concentration used in the experiment shown in FIG. 5, the unmodified peptides still did not show any effect, whereas the two modified nona- and hepta-peptides (thiolactone-containing GDSVc[CASYF] (SEQ ID NO: 17) and SVc[CASYF]) (SEQ ID NO: 18) seemed to cause a very small stimulatory effect (Table 2).

3.2 Purification and Analysis of the Delta-toxin of S. epidermidis Tü3298

The delta-toxin of S. epidermidis Tü3298 was purified to homogeneity in a single-step procedure (for preparative and analytical HPLC analysis of delta-toxin see Experimental procedures). ESI-MS revealed a mass of 2448 u+/− 0.7. This is almost precisely 28 u more than the calculated mass of the translation product (2419.4 u), suggesting a formylation of the N-terminal methionine. This was supported by the observation that sequencing by automated Edman degradation required an unusually high amount of peptide. It was probably due to an incomplete modification of the peptide, that the N-terminal amino acid sequence could be determined that confirmed the expected sequence.

3.3 The Effect of *S. epidermidis* agr Peptides on agr-expression in *Staphylococcus aureus*—measured by Delta-toxin Production The agr inhibiting activity of the peptides (listed in FIG. 2) for *S. aureus* was investigated. In both *S. epidermidis* and *S. aureus*, the delta-toxin is encoded within the RNAIII region, which appears to be the regulatory molecule of the agr system (Janzon et al., 1989; Otto et al., 1998). Previously, the activity of the agr system was usually measured by quantifying RNAIII expression by Northern blot analysis. Since delta-toxin is translated from RNAIII and since its production is responsive to added pheromone we developed an assay based on quantification of the delta-toxin by HPLC.

The quantification of the delta-toxin by HPLC represents a fast and precise assay. A Resource PHE column and a water/acetonitrile gradient allowed many samples to be passed through without the column becoming blocked and offered the advantage that most proteins and peptides passed through the column, whereas the extremely amphiphilic alpha-helical delta-toxin eluted as a distinct peak. Using the supernatant of the *S. epidermidis* test strain Tü3298, this peak was identified as the delta-toxin by mass spectrometry and by testing for synergistic hemolysis (data not shown).

The HPLC delta-toxin assay was used to screen for *S. aureus* strains that produced delta-toxin, which indicates that the agr system is active in these strains. The delta-toxin-negative strain *S. aureus* RN4220 was used as a control. Of eight strains tested, four produced delta-toxin (Table 3). DNA sequencing of agrD showed that the pheromone peptide of each of the positive strains belonged to the *S. aureus* agr pheromone subgroup I (pheromone peptide sequence: YSTCDFIM). For the agr inhibition tests, *S. aureus* strains Newman and 8325-4 were chosen.

3.4 Activity of the *S. epidermidis* Pheromone Peptides

The delta-toxin assay was used to test for a potential inhibitory activity of the *S. epidermidis* pheromone on the agr system of *S. aureus*. It was shown that at different concentrations from 0.05 to 1 μM the following synthetic peptides with an intramolecular cyclic structure suppress the synthesis of delta-toxin in *S. aureus* Newman after 8 h of growth (FIG. 5).

DSVc[CASYF] (SEQ ID NO: 19)
GDSVc[CASYF] (SEQ ID NO: 17)
SVc[CASYF] (SEQ ID NO: 18)
DSVc[SASYF] (SEQ ID NO: 19)
DSVc[XASYF] (SEQ ID NO: 19)

The thiolactone-containing hepta-, octa-, and nonapeptides were most active, but also the peptides containing lactone and lactam structures exhibited considerable activity. The lactone- and lactam-containing peptides (DSVC[SASYF] (SEQ ID NO: 19) and DSVC[XASYF] (SEQ ID NO: 19) see above) were unable to activate the *S. epidermidis* agr system, as shown by the results of CAT assays, nor was delta-toxin production inhibited. The inhibition of the *S. aureus* agr system is less dependent on a thiolactone structure and a correct N-terminus of the *S. epidermidis* pheromone, whereas activation of the *S. epidermidis* agr system depends on the presence of the thiolactone-containing octapeptide with the aspartate residue at the N-terminus. The 20 linear peptides DSVXASYF (SEQ ID NO: 19) (linear peptides where X represents each one of the biogenic amino acids) showed no activity.

Furthermore, it should be noted that the addition of the pheromone or its derivatives did not affect bacterial growth in any of the assays described in this specification.

3.5 The Effect of *S. epidermidis* agr Peptides on Agr-expression in *Staphylococcus aureus*—measured by Alpha-toxin and Protein A Production The *S. aureus* agr system regulates the production of certain exoproteins and surface-associated proteins. In most cases, the exoproteins are up-regulated and the surface-associated proteins are down-regulated (Recsei et al., 1986). The effect of the synthetic cyclic peptides on the production pattern of surface-associated proteins and exoproteins was investigated (for Exoprotein analysis of *S. epidermidis* see Experimental procedures).

Figures 6A, 6B:
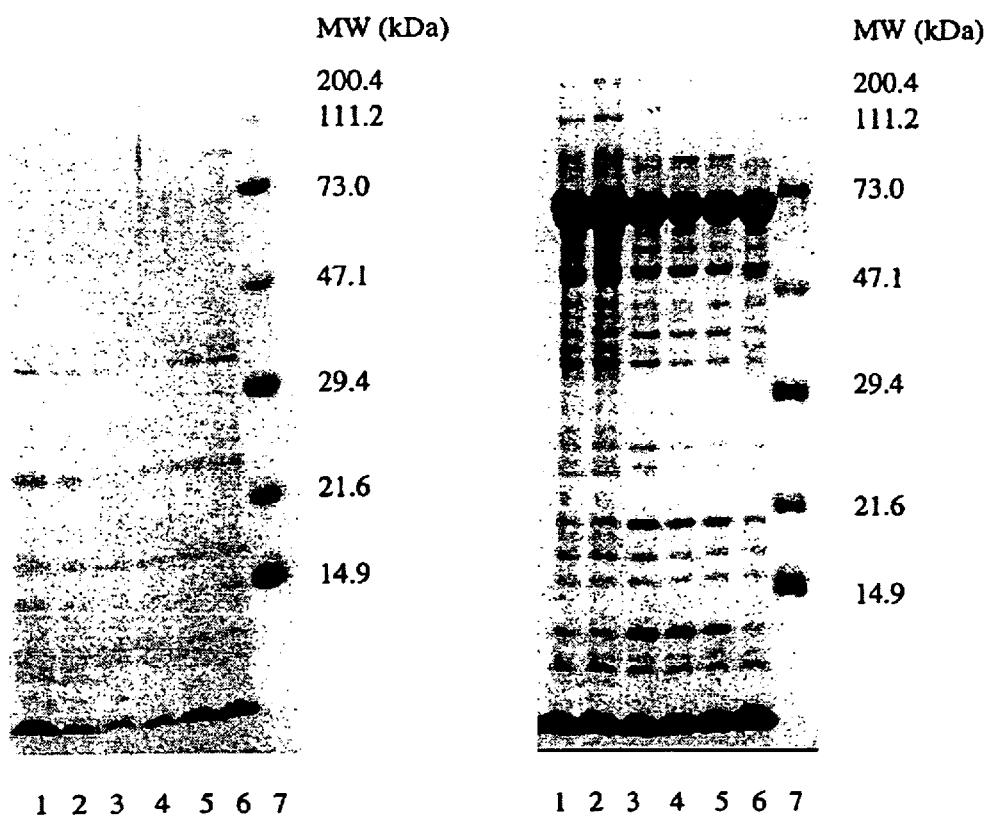
FIG. 6: Influence of the S. epidermidis pheromone and its derivatives on the production of exoproteins and surface-associated proteins in S. aureus Newman. (A) Exoproteins: basic medium was inoculated with 1/100 vol. of a preculture of S. aureus Newman. At the same time, the pheromone or one of its derivatives was added at a concentration of 1 µM. The peptides were dissolved in DMSO (dimethylsulfoxide); a control received only DMSO. Culture filtrates (20 µl) of the cultures harvested after 16 h of growth were applied to Tricine SDS-PAGE and stained with Coomassie Blue. (B) Surface-associated proteins: pellets of the centrifuged 16 h cultures were dissolved in SDS-PAGE loading buffer containing 1% SDS, boiled at 1000C for 5 min, and applied to Tricine SDS-PAGE after removal of insoluble material by centrifugation. Lanes: (1) lactam-containing octapeptide DSVC[XASYF] (SEQ ID NO: 19); (2) lactone-containing octapeptide DSVc[SASYF] (SEQ ID NO: 19); (3) thiolactone-containing SVc[CASYF] (SEQ ID NO: 18); (4) synthetic S. epidermidis pheromone, DSVC[CASYF] (SEQ ID NO: 19); (5) thiolactone-containing GDSVC[CASYF] (SEQ ID NO: 17); (6) control (with DMSO); (7) molecular weight standards.

The synthetic cyclic peptides were added at a concentration of 1 μM to a culture that was inoculated by 1/100 vol. of a preculture; the cultures were incubated for 16 h. The reduction of exoprotein production was most pronounced with the peptides that were also effective inhibitors of delta-toxin production, i.e., the natural pheromone peptide and., the modified peptides SVc[CASYF](SEQ ID NO: 18) and GDSVc[CASYF] (SEQ ID NO: 17) (FIG. 6A). Certain surface-associated proteins were synthesized in higher amounts after addition of these peptides (FIG. 6B) The same effects were also observed with the lactone- and lactam-containing peptides, but the effects were less pronounced, which is in agreement with the results of the delta-toxin test.

Figure 7A:
FIG. 7: Influence of the S. epidermidis pheromone and its derivatives on alpha-toxin production and protein A production in S. aureus Newman. (A) Immunoblot with anti-alpha-toxin antiserum. Basic medium was inoculated with 1/100 vol. of a preculture of S. aureus Newman. At the same time, the pheromone or one of its derivatives was added at a concentration of 1 µM. The peptides were dissolved in DMSO; a control received only DMSO. Culture filtrate (20 µl) of the cultures harvested after 16 h of growth was applied to Tricine SDS-PAGE. Immunoblotting and development are described in the Experimental Procedures. (B) Immunoblot with anti-protein A antiserum. For protein A detection, the cell pellets of the 16 h cultures (see above) were treated with lysostaphin to release the covalently attached protein A from the cell surface. After centrifugation, the supernatant was applied to Tricine SDS-PAGE. Immunoblotting and development are described in the Experimental Procedures. Lanes: (1) control (with DMSO); (2) thiolactone-containing GDSVc[CASYF] (SEQ ID NO: 17); (3) synthetic S. epidermidis pheromone, DSVc [CASYF] (SEQ ID NO: 19); (4) thiolactone-containing SVc[CASYF] (SEQ ID NO: 18); (5) lactone-containing octapeptide DSVc[SASYF] (SEQ ID NO: 19); (6) lactam-containing octapeptide DSVc[XASYF] (SEQ ID NO: 19).
Figure 7B:

An immunoblot of surface protein samples with antiserum raised against protein A, as an example of a surface protein known to be down-regulated by the agr system, showed the expected increased levels of protein A production in the samples to which the thiolactone-containing derivatives of the *S. epidermidis* pheromone had been added (FIG. 7A). In the control, no protein A was detected. The addition of the lactone- and lactam-containing cyclic peptides led to detectable protein A production, but to a lesser extent than that of the thiolactone-containing peptides. An immunoblot (for Immunoblots see Experimental procedures) of the exoprotein samples with antiserum raised against alpha-toxin, known to be up-regulated by the agr system, gave the expected opposite results (FIG. 7B). The synthetic and modified derivatives of the *S. epidermidis* pheromone led to a decreased production of the delta-toxin and of the alpha-toxin, one of the most important virulence factors of *S. aureus*.

Due to the capacity of the inventive peptides for blocking the formation of important virulence factors of *S. aureus*, these peptides are useful in treating Staphylococcus infections. Such kind of infections play a crucial role in several kind of diseases and disorders, including cancer and further diseases especially concerning the immune system. The administering of the inventive peptides to treat said kind of diseases and disorders may be done in usual ways, preferably oral or intravenous. Another application of the inventive peptides is the use for vaccination to prevent said kind of infections. In another preferred embodiment of the invention the nucleic acid sequences encoding the inventive peptides are administered.

Experimental Procedures

DNA sequence analysis—DNA was sequenced by cycle sequencing on a DNA sequencer 4000 L (LI-COR Inc., Lincoln, Nebr.) using the Thermo Sequenase fluorescent-labeled prime cycle sequencing kit (Amersham, Little Chalfont, UK). All fluorescent-labeled primers were purchased from MWG-Biotech (Ebersberg, Germany).

Synthesis of peptides—The linear and cyclic peptides SVCASYF/DSVCASYF/GDSVCASYF) (SEQ ID NOs:

18,19,17) were synthesized manually using the fluorenyl-methoxycarbonyl (Fmoc) protocol for solid phase synthesis. All amino acids were from Novabiochem (Laufelingen, Switzerland) A Trityl-resin (PepChem—Clausen and Goldammer, Tubingen, Germany) was loaded with Fmoc-phenylalanine residue used as solid support. Resin substitution was 0.7 mmol/g and 0.1 mmol amino acid was used for each coupling. The tert-butyl group was used to protect serine and tyrosine residues. For linear peptides, a trityl-group and for cyclised peptides a methoxytrityl group (Mmt) was used to protect cysteine residues. The amino acids were coupled using 2-(lH-benzotriazole-1-yl)-1,1,3,3-tetramethyluronium tetrafluoroborate and hydroxybenzot-riazole (TBTU/HOBt). Deprotection of the Fmoc-amino acid attached to the resin was accomplished by using piperidine. For the N-terminal amino acids, Boc(tert-butyloxycarbonyl)-protection was used. Linear peptides were directly cleaved with TFA:TIS (triisopropylsilane) (95:5). The synthesis route for cyclic peptides comprised cleavage of the peptides from the resin and removal of the Mmt-group performed in a one step procedure by using DCM (dichloromethane):TFA:TIS (94:1:5) for 15 min. The filtrates were evaporated, dissolved in DCM and cyclised with DCC (dicyclohexylcarbodiimide)/DMAP (4-dimethylaminopyridine) (3eq.) for 12 h (Neises and Steglich, 1978). The solvents were then evaporated and the other protecting groups were finally cleaved with TFA:water (90:10) for 2 h. The TFA was removed and the peptides were dissolved in acetonitrile:water (1:1). The solutions were filtered and purified by preparative HPLC. The HPLC-fractions were collected and lyophilised. Purity of peptides was confirmed by HPLC and ESI-mass spectrometr.

Electrospray mass spectrometry—ESI-MS was performed on an API III TAGA Triple Quadrupole (Perkin Elmer Sciex, Thornhill, Ontario, Canada). Samples were dissolved in acetonitrile/water (1:1, vol/vol) and introduced into the ion source at a constant flow rate of 70 µl/min. The orifice voltage was set at 80 V.

Plasmids—The promoter test plasmid pRB594 is a derivative of pRB373 (Bruckner, 1992). It contains the promoterless pUB112 cat gene (Bruckner and Matzura, 1985) adjacent to a multiple cloning site and carries the erythromycin resistance gene ermB from transposon Tn551. Plasmid pRB594P3 was constructed by insertion of a BamHI-digested PCR product of the agr P3 region of S. epidermidis ATCC 14990 into the BazHI site of the multiple cloning site (Otto et al., 1998).

Chloramphanicol acetyltran3ferase (CAT) assay—CAT activity was determined according to the method of Shaw (Shaw, 1975). The assay mixture contained 100 MM Tris/HCl (pH 7.8), 0.1 mM Acetyl-Coenzyme A, and 0.4 mg/ml 5,5'-dithiobis-2-nitrobenzoic acid (DTNB). Assays were performed in 96 well microtitre plates using a SpectraMax 340 microtitre plate reader (Molecular Devices, Sunnyvale, Calif.) with SpectraMaxPro software. 5 µl cell extract and 5 µl 5 mM chloramphenicol in 100% ethanol (or 5 µl 100% ethanol in controls) were added to 90 µl of the assay mixture. Cell extracts were diluted 1:10 or 1:100 with 20 mM Tris/HCl (pH 7.8) when necessary. Absorption at 412 nm was measured every 15 s for 20 min. The linear part of the resulting curve was used to determine the CAT activity (absorption coefficient epsilon=13600 1/M for DTNB). For calculation of the specific activity, protein contents of the cell extracts were determined using the Bio-Rad DC protein assay for detergent-containing samples (Bio-Rad Laboratories GmbH, Munich, Germany).

Preparative and analytical UPLC analysis of delta-toxin and of linear and cyclic peptides—Crude peptides were isolated on a Waters 600 Multi Solvent Delivery System equipped with a Lambda Max Model 481 as detector. A semi-preparative column (Nucleosil C18, 4×250 mm; 5 µm; Grom, Herrenberg, Germany) was eluted at a flow rate of 3.5 ml/min with a linear gradient [10–100% B in A in 45 min; solvent A: 0.1% TFA (trifluoroacetic acid) in water; solvent B: 0.1% TFA in acetonitrile]; the detection wavelength was 214 nm. The concentration of purified peptides, redissolved in DMSO (dimethylsulfoxide), was determined using analytical HPLC on a Kontron HPLC system with Kroma System 2000 software. An analytical column (Spherisorb ODS2 2×100 mm; 5 µm; Grom, Herrenberg, Germany) was eluted at a flow rate of 250 µl/min with a linear gradient (0–100% B in A in 30 min; solvent A: 0.1% TFA in water; solvent B: 0.1% TFA in acetonitrile); the detection wavelength was 214 nm. A known amount of the (unmodified) peptide DSVc[CASYF] was used as a reference. The amount of delta-toxin was quantified using the same system. A Pharmacia Resource PHE 1-ml column was eluted with 1.5 column volumes of a linear gradient (0–100 % of B in A; A: 0.1% TFA from water; B: 0.1% TFA in acetonitrile). The S. epidermidis delta-toxin was eluted using the same conditions on an ÄKTA explorer 100 system (Amersham Pharmacia Biotech, Freihurg, Germany); the isolated delta-toxin was chemically analyzed by ESI-MS.

Exoprotein analysis of S. epidermidis—Cells were grown in TSB (tryptic soy broth) or BM ["basic medium": 1% tryptone (Difco), 0.5% yeast extract (Gibco BRL), 0.5!k NaCl, 0.1% $K_2HPO_4$, 0.1% glucose]. Staphylococcal cells were disrupted in 20 MM Tris/HCl (pH 7.8) by glass beads. Cell debris were removed by centrifugation (10 min, 5,000× g). Membrane fractions were prepared by additional ultra-centrifugation at 105,000×g for 1 h. Surface-associated proteins were isolated by boiling cells at 100° C. for 5 min; surface proteins were isolated by incubating cells with lysostaphin for 10 min at 37° C. Chromosomal staphylococcal DNA was prepared according to the method of Mamur (Mamur, 1961). Proteins were separated by Tricine-SDS-PAGE according to Schägger and Jagow (Schägger and Jagow, 1987) using BioRad Protean IIxi chambers and a separation length of 16 cm.

Immunoblots—SDS-polyacrylamide gels were blotted onto nitrocellulose membranes (Schleicher and Schuell BA 83) using the semi-dry blotting technique. Blots were blocked overnight with So skim milk. The first antibody was applied for 2 h at a concentration of 1:20,000 (anti-alpha-toxin) or 1:40,000 (anti-protein A). After washing, the blots were incubated with anti-IgG-coupled HRP (horseradish peroxidase) from Amersham Pharmacia (1:5,000) for 1 h. All dilutions were made in TBS (Tris-buffered saline: 10 mM Tris/HCl, pH 7.4, 150 EM NaCl). Signals were detected with the ECL detection system (Amersham Pharmacia Biotech, Freiburg, Germany).

Reference

Brückner, R. (1992). A series of shuttle vectors for Bacillus subtilis and Escherichia coli. Gene 122, 187–192.

Brückner, R., and Matzura, H. (1985). Regulation of the inducible chloramphenicol acetyltransferase gene of Staphylococcus aureus plasmid pUB112. EMBO J. 4, 2295–2300.

Janzon, L., Löfdahl, S., and Arvidson, S. (1989). Identification and nucleotide sequence of the delta-lysin gene, hid, adjacent to the accessory gene regulator (agr) of Staphylococcus aureus. Mol. Gen. Genet. 219, 480–485.

Ji, G., Beavis, R., and Novick, R. P. (1997). Bacterial interference caused by autoinducing peptide variants. Science 276, 2027–30.

Ji, G., Beavis, R. C., and Novick, R. P. (1995). Cell density control of staphylococcal virulence mediated by an octapeptide pheromone. Proc. Natl. Acad. Sci. U S A 92, 12055–12059.

Mamur, J. (1961). A procedure for the isolation of deoxyribonucleic acid from microorganisms. J. Mol. Biol. 3, 208–218.

Neises, B., and Steglich, W. (1978). Einfaches Verfahren zur Veresterung von Carbonsäuren. Angew. Chem. 90, 556–557.

Novick, R. P., Projan, S. J., Kornblum, J., Ross, H. F., Ji, G., Kreiswirth, B., Vandenesch, F., and Moghazeh, M. (1995). The agr P2 operon: an autocatalytic sensory transduction system in *Staphylococcus aureus*. Mol. Gen. Genet. 248, 446–458.

Novick, R. I., Ross, H. F., Pro-an, S. J., Kornblum, J., Kreiswirth, B., and Moghazeh, S. (1993). Synthesis of staphylococcal virulence factors is controlled by a regulatory RNA molecule. EMBO J. 12, 3967–3975.

Otto, M., Süβmuth, R., Jung, G., and Götz, F. (1998). Structure of the pheromone peptide of the *Staphylococcus epdermidis* agr system. FEBS Letters 424, 89–94.

Peng, H. L., Novick, R. P., Kreiswirth, B., Kornblum, J., and Schlievert, P. (1988). Cloning, characterization, and sequencing of an accessory gene regulator (agr) in *Staphylococcus aureus*. J. Bacteriol. 170, 4365–72.

Recsei, P., Kreiswirth, B., O'Reilly, M., Schlievert, P., Gruss, A., and Novick, R. P. (1986). Regulation of exoprotein expression in *Staphylococcus aureus* by agr. Mol. Gen. Genet. 202, 58–61.

Schägger, H., and Jagow, G. (1987). Tricine-sodium dodecyl sulfate-polyacrylamide gel electrophoresis for the separation of proteins in the range from 1 to 100 kDa. Anal. Biochem. 166, 368–379.

Shaw, W. V. (1975). Chloramphenicol acetyltransferase from chloramphenicol-resistant bacteria. Methods Enzymol. 43, 737–755.

What is claimed is:

1. A peptide comprising the following amino acid sequence
S V X A S Y F (SEQ ID NO: 18),
wherein X is a serine.

2. The peptide according to claim 1, wherein an intramolecular cyclic bond with a lactone structure is located between the central serine and the C-terminal carboxy group.

3. The peptide according to claim 2, wherein the carbonyl (C=O)-group of the C-terminal carboxy group is replaced by a methylene (CH$_2$)-group.

4. The peptide according to claim 2, wherein in the intramolecular cyclic bond, the sulfur atom, the oxygen atom or the NH-group is replaced by a methylene (CH$_2$)-group.

5. A peptide comprising the following amino acid sequence
S V X A S Y F (SEQ ID NO:18),
wherein X is 1,3-diamino-propionic acid.

6. The peptide according to claim 5, wherein an intramolecular cyclic bond with a lactam structure is located between the central 1,3-diaminopropionic acid and the C-terminal carboxy group.

7. The peptide according to claim 6, wherein the carbonyl (C=O)-group of the C-terminal carboxy group is replaced by a methylene (CH$_2$)-group.

8. The peptide according to claim 6, wherein in the intramolecular cyclic bond, the sulfur atom, the oxygen atom or the NH-group is replaced by a methylene (CH$_2$)-group.

9. A peptide comprising the following amino acid sequence
S V C A S Y F (SEQ ID NO:18),
wherein an intramolecular cyclic bond with a thiolactone structure is located between the central cysteine and the C-terminal carboxy group.

10. The peptide according to claim 9, wherein the carbonyl (C=O)-group of the C-terminal carboxy group is replaced by a methylene (CH$_2$)-group.

11. The peptide according to claim 9, wherein in the intramolecular cyclic bond, the sulfur atom, the oxygen atom or the NH-group is replaced by a methylene (CH$_2$)-group.

12. A peptide comprising the following amino acid sequence
S V C A S Y F (SEQ ID NO:18),
wherein said peptide is a cyclic heptapeptide having the amino acid sequence
S V c[C A S Y F] (SEQ ID NO:18).

13. A peptide comprising the following amino acid sequence,
S V C A S Y F (SEQ ID NO:18),
wherein said peptide is a cyclic octapeptide having the amino acid sequence
D S V c [C A S Y F] (SEQ ID NO:19).

14. A peptide comprising the following amino acid sequence,
S V S A S Y F (SEQ ID NO:18),
wherein said peptide is a cyclic octapeptide having the amino acid sequence
D S V c [S A S Y F] (SEQ ID NO:19).

15. A peptide comprising the following amino acid sequence,
S V X A S Y F (SEQ ID NO:18),
wherein X is 1,3-diamino-propionic acid and said peptide is a cyclic octapeptide having the amino acid sequence
D S V c [X A S Y F] (SEQ ID NO:19), wherein X is 1,3-diamino-propionic acid.

16. A peptide comprising the following amino acid sequence,
S V C A S Y F (SEQ ID NO:18),
wherein said peptide is a cyclic nonapeptide having the amino acid sequence
G D S V c[C A S Y F] (SEQ ID NO:17).

* * * * *

SEQUENCE LISTING

<160> NUMBER OF SEQ ID NOS: 21

<210> SEQ ID NO 1
<211> LENGTH: 3528
<212> TYPE: DNA
<213> ORGANISM: Staphylococcus epidermidis

<400> SEQUENCE: 1

```
aagccgtgag cttgggagag actcacggct tgataactta ttattaaggg aatgtttta      60 cagttatttt ttcaatctat tttttgggga tgttattaat tatgaaaaaa tttttagtga    120
atttatctat ttaacatgat aaattgaatg ttgtttacga tagcttacat gctagaaata    180
attacctatt taaggtagct aagaataata cgtaacactg agtccaagga aactacagct    240
actagcaaat gcttctcact tgcttagttt atattagtaa attattaagt tgggatggct    300
caacaactca ctaataatat taattatacg aagaaaacaa agttacaaaa gttacaatag    360
actcattcaa aaattatttt ttgaatttat taactgtatc gataatccat tttactaaat    420
caccgattgt agaaatgata tctgctgcca ttataacttc actcctttcg aattaaggta    480
atggatacga atgaatttaa cattcactcg actagattaa gcaattttt caactatctt      540 tcaatcacat cactgtgata tgagtctatt aaaacatgat ttttccattt aaagattaaa    600
atttcgtaaa tagcaatatt tagtactcaa ctgtaaaact aaatatggta aaatatctaa    660
tagtacttaa ttaaaacact taggtatatt ttttaacag ttaggcatgc tttctaaaaa     720
atgttgcgca aaattgtata atgacacttg aggagagtag taaacaagtg aaaatcatcg    780
ataaaaaaat tgagcaattt gctcatattt acaacgtacg taaaaataac ttagatcaca    840
tacagtttct aaaaattcgt ttagggatgc aggtactagc gataaatatt gaaaagtcta    900
tagttgtgta tgggctagca ataatctttc atactttctt ttacacactt ttaactcatt    960
taagttattt tttaattagg agacatgcac acggtacgca tgcaaattcg tcattgttat   1020
gtcatattca gaacataatt ttctttatta tctttccata cttaataata aagttagata   1080
ttaactattt tgttctttta tctatggcat tagtcggatt aattattacc attttatacg   1140
cacctgcagc aactaagaaa caacctatac ctagacgtct tgtaaagcga aaaaaaatac   1200
tctccatatt tttatattgt actatcgtag ttatttcatt agtaactaaa gaaccggtaa   1260
```

-continued

```
ataaacttat tttattcggt gtaattttag aatctttaac attactaccc atctttttcc    1320
ctaaggagga tattaatcat ggaaatcatt tttaatttat ttataaaatt tttcactaca    1380
atcttggaat ttattggtac tgtagcagga gatagtgtat gtgcctctta ctttgacgaa    1440
ccagaagtac cagaagaact gactaaacta tacgagtaaa tataacccta gaaagtgtgt    1500
aagatatgga tgatattaat ctatttccgt ttgcaggcct acaaatcttt ttaatgattt    1560
gggttactaa agttatcatt aatatgaaat ttaattttag ggattacata atcgttttta    1620
cgattgtaat cccttctgca ataatgtatt acttttggca agtaaagca ttaatagttt    1680 tggttataat aatcaccatt ttcttttata caaaaataaa gctttattca atattagttg    1740
tattattcac cactatgatc ttatatataa ctaatttcat aactgtatac atacatttga    1800
ctataaaaga ttatattccg tttaaatttg ctttacagtt aatacatttt acctcttttg    1860
taatcataac tctaattatt gcttatttaa ctcaactatt gttcaataaa ttaaaagtat    1920
cctacttgtc actcaataaa agatacttat tgataataac aatagtactt ttcatatcat    1980
ttattttact ttatatggtg tcacaaactg atatgcgagg aaatgatacc cttaaattat    2040
atgccatctt attgttgggt attatggttt ttttaagtgt agtgatatta gtgatgtcca    2100
attttacact ccgtgaaatg aggtataaac gtaatgtaaa agaaatcgaa gcatattatg    2160
agtacacgtt acgtatagaa agcattaaca atgaaatgcg taagttccga catgattatg    2220
tgaatatcct caccactctt tcagattaca ttagagaaga tgatatgcct ggattacgta    2280 aatatttttaa tgaaatatc gttccaatga agataaatt aaaaactcgc tctattaaaa    2340
tgaatggtat tgaaaagttg aaagtgagag aaattaaagg gctgattact actaaaatta    2400
ttcaagctca agaaaaacgt attccaatta gtattgaggt tcctgatgaa attgatcgta    2460
tcgatatgaa tactgttgag cttagtcgta ttatcggtat tatagttgat aatgctattg    2520
aagcttcaga aaatcttgag gaaccactca tcaatatcgc attcatcgat aatgaggaat    2580
ctgtcacttt tatcgttatg aataaatgta gtaatgatat ccctaaaatt catgagttgt    2640
ttgaacaagg ttttttctact aaaggtgata atcgcggttt aggtttatca actttaaaag    2700
aactgacaga ctcaaacgag aatgttttat tagatactgt catcgaaaat ggttactttg    2760
tacaaaaagt agaaataaat aataaggaat cataaggatg tgtagaatta aatgaaaatt    2820
tttgtttgtg aagatgacca aagacaaaga gaacatatgg tatcaatcat taaaaactac    2880
ataatgattg aagaaaagcc aatggagtta gctttacgaa caaatgatcc ttatgaggtc    2940
ttagagcaat caaaagaact taatgacatt ggttgttact tccttgatat tcaattagaa    3000
gctgatatga acggtattaa attagccagt gaaattcgta acatgatcc tgttggtaat    3060 attatatttg taaccagtca cagtgagctg acttatttga cgtttgttta taaagtggct    3120
gctatggatt ttattttttaa agatgatcca tctgaattaa aaatgagaat catagattgt    3180
cttgaaacag cacatacaag actcaaaatta ttatcaaaag aaagtaatgt agatacgatt    3240 gagtaaagc ggggaagtaa ttcagtatac gttcaatatg atgatattat gttttttgaa    3300
tcatctacga aatctcatag actcattgca catcttgata atcgacaaat tgaattttat    3360
ggaaatttaa aggaattagc acagcttgat gaacgtttct ttagatgtca taacagtttt    3420
gtaataaaca ggcataatat tgaatctatt gactcaaaag aacgtattgt ttactttaag    3480
aatggcgaaa attgtttcgc ttcagtacgt aatgttaaaa aaatataa                 3528
```

<210> SEQ ID NO 2
<211> LENGTH: 195

```
<212> TYPE: PRT
<213> ORGANISM: Staphylococcus epidermidis
<220> FEATURE:
<223> OTHER INFORMATION: agrB
<221> NAME/KEY: VARIANT
<222> LOCATION: (1)
<223> OTHER INFORMATION: nucleic acid triplet 'gtg' codes for amino acid
      'MET'

<400> SEQUENCE: 2

Met Lys Ile Ile Asp Lys Lys Ile Glu Gln Phe Ala His Ile Tyr Asn
  1               5                  10                  15

Val Arg Lys Asn Asn Leu Asp His Ile Gln Phe Leu Lys Ile Arg Leu
                 20                  25                  30

Gly Met Gln Val Leu Ala Ile Asn Ile Glu Lys Ser Ile Val Val Tyr
             35                  40                  45

Gly Leu Ala Ile Ile Phe His Thr Phe Phe Tyr Thr Leu Leu Thr His
         50                  55                  60

Leu Ser Tyr Phe Leu Ile Arg Arg His Ala His Gly Thr His Ala Asn
 65                  70                  75                  80

Ser Ser Leu Leu Cys His Ile Gln Asn Ile Ile Phe Phe Ile Ile Phe
                 85                  90                  95

Pro Tyr Leu Ile Ile Lys Leu Asp Ile Asn Tyr Phe Val Leu Leu Ser
                100                 105                 110

Met Ala Leu Val Gly Leu Ile Ile Thr Ile Leu Tyr Ala Pro Ala Ala
            115                 120                 125

Thr Lys Lys Gln Pro Ile Pro Arg Arg Leu Val Lys Arg Lys Lys Ile
        130                 135                 140

Leu Ser Ile Phe Leu Tyr Cys Thr Ile Val Val Ile Ser Leu Val Thr
145                 150                 155                 160

Lys Glu Pro Val Asn Lys Leu Ile Leu Phe Gly Val Ile Leu Glu Ser
                165                 170                 175

Leu Thr Leu Leu Pro Ile Phe Phe Pro Lys Glu Asp Ile Asn His Gly
                180                 185                 190

Asn His Phe
        195

<210> SEQ ID NO 3
<211> LENGTH: 46
<212> TYPE: PRT
<213> ORGANISM: Staphylococcus epidermidis
<220> FEATURE:
<223> OTHER INFORMATION: agrD

<400> SEQUENCE: 3

Met Glu Ile Ile Phe Asn Leu Phe Ile Lys Phe Phe Thr Thr Ile Leu
  1               5                  10                  15

Glu Phe Ile Gly Thr Val Ala Gly Asp Ser Val Cys Ala Ser Tyr Phe
                 20                  25                  30

Asp Glu Pro Glu Val Pro Glu Glu Leu Thr Lys Leu Tyr Glu
             35                  40                  45

<210> SEQ ID NO 4
<211> LENGTH: 429
<212> TYPE: PRT
<213> ORGANISM: Staphylococcus epidermidis
<220> FEATURE:
<223> OTHER INFORMATION: agrC

<400> SEQUENCE: 4
```

-continued

```
Met Asp Asp Ile Asn Leu Phe Pro Phe Ala Gly Leu Gln Ile Phe Leu
 1               5                  10                  15

Met Ile Trp Val Thr Lys Val Ile Ile Asn Met Lys Phe Asn Phe Arg
             20                  25                  30

Asp Tyr Ile Ile Val Phe Thr Ile Val Ile Pro Ser Ala Ile Met Tyr
         35                  40                  45

Tyr Phe Trp Gln Ser Lys Ala Leu Ile Val Leu Val Ile Ile Ile Thr
     50                  55                  60

Ile Phe Phe Tyr Thr Lys Ile Lys Leu Tyr Ser Ile Leu Val Val Leu
65                  70                  75                  80

Phe Thr Thr Met Ile Leu Tyr Ile Thr Asn Phe Ile Thr Val Tyr Ile
                 85                  90                  95

His Leu Thr Ile Lys Asp Tyr Ile Pro Phe Lys Phe Ala Leu Gln Leu
             100                 105                 110

Ile His Phe Thr Ser Phe Val Ile Ile Thr Leu Ile Ile Ala Tyr Leu
         115                 120                 125

Thr Gln Leu Leu Phe Asn Lys Leu Lys Val Ser Tyr Leu Ser Leu Asn
    130                 135                 140

Lys Arg Tyr Leu Leu Ile Ile Thr Ile Val Leu Phe Ile Ser Phe Ile
145                 150                 155                 160

Leu Leu Tyr Met Val Ser Gln Thr Asp Met Arg Gly Asn Asp Thr Leu
                165                 170                 175

Lys Leu Tyr Ala Ile Leu Leu Leu Gly Ile Met Val Phe Leu Ser Val
            180                 185                 190

Val Ile Leu Val Met Ser Asn Phe Thr Leu Arg Glu Met Arg Tyr Lys
        195                 200                 205

Arg Asn Val Lys Glu Ile Glu Ala Tyr Tyr Glu Tyr Thr Leu Arg Ile
    210                 215                 220

Glu Ser Ile Asn Asn Glu Met Arg Lys Phe Arg His Asp Tyr Val Asn
225                 230                 235                 240

Ile Leu Thr Thr Leu Ser Asp Tyr Ile Arg Glu Asp Asp Met Pro Gly
                245                 250                 255

Leu Arg Lys Tyr Phe Asn Glu Asn Ile Val Pro Met Lys Asp Lys Leu
            260                 265                 270

Lys Thr Arg Ser Ile Lys Met Asn Gly Ile Glu Lys Leu Lys Val Arg
        275                 280                 285

Glu Ile Lys Gly Leu Ile Thr Thr Lys Ile Ile Gln Ala Gln Glu Lys
    290                 295                 300

Arg Ile Pro Ile Ser Ile Glu Val Pro Asp Glu Ile Asp Arg Ile Asp
305                 310                 315                 320

Met Asn Thr Val Glu Leu Ser Arg Ile Ile Gly Ile Val Asp Asn
                325                 330                 335

Ala Ile Glu Ala Ser Glu Asn Leu Glu Glu Pro Leu Ile Asn Ile Ala
            340                 345                 350

Phe Ile Asp Asn Glu Glu Ser Val Thr Phe Ile Val Met Asn Lys Cys
        355                 360                 365

Ser Asn Asp Ile Pro Lys Ile His Glu Leu Phe Glu Gln Gly Phe Ser
    370                 375                 380

Thr Lys Gly Asp Asn Arg Gly Leu Gly Leu Ser Thr Leu Lys Glu Leu
385                 390                 395                 400

Thr Asp Ser Asn Glu Asn Val Leu Leu Asp Thr Val Ile Glu Asn Gly
                405                 410                 415

Tyr Phe Val Gln Lys Val Glu Ile Asn Asn Lys Glu Ser
```

420              425

<210> SEQ ID NO 5
<211> LENGTH: 238
<212> TYPE: PRT
<213> ORGANISM: Staphylococcus epidermidis
<220> FEATURE:
<223> OTHER INFORMATION: agrA

<400> SEQUENCE: 5

Met Lys Ile Phe Val Cys Glu Asp Asp Gln Arg Gln Arg Glu His Met
  1               5                  10                  15

Val Ser Ile Ile Lys Asn Tyr Ile Met Ile Glu Glu Lys Pro Met Glu
             20                  25                  30

Leu Ala Leu Arg Thr Asn Asp Pro Tyr Glu Val Leu Glu Gln Ser Lys
         35                  40                  45

Glu Leu Asn Asp Ile Gly Cys Tyr Phe Leu Asp Ile Gln Leu Glu Ala
     50                  55                  60

Asp Met Asn Gly Ile Lys Leu Ala Ser Glu Ile Arg Lys His Asp Pro
 65                  70                  75                  80

Val Gly Asn Ile Ile Phe Val Thr Ser His Ser Glu Leu Thr Tyr Leu
                 85                  90                  95

Thr Phe Val Tyr Lys Val Ala Ala Met Asp Phe Ile Phe Lys Asp Asp
            100                 105                 110

Pro Ser Glu Leu Lys Met Arg Ile Ile Asp Cys Leu Glu Thr Ala His
        115                 120                 125

Thr Arg Leu Lys Leu Leu Ser Lys Glu Ser Asn Val Asp Thr Ile Glu
    130                 135                 140

Leu Lys Arg Gly Ser Asn Ser Val Tyr Val Gln Tyr Asp Asp Ile Met
145                 150                 155                 160

Phe Phe Glu Ser Ser Thr Lys Ser His Arg Leu Ile Ala His Leu Asp
                165                 170                 175

Asn Arg Gln Ile Glu Phe Tyr Gly Asn Leu Lys Glu Leu Ala Gln Leu
            180                 185                 190

Asp Glu Arg Phe Phe Arg Cys His Asn Ser Phe Val Ile Asn Arg His
        195                 200                 205

Asn Ile Glu Ser Ile Asp Ser Lys Glu Arg Ile Val Tyr Phe Lys Asn
    210                 215                 220

Gly Glu Asn Cys Phe Ala Ser Val Arg Asn Val Lys Lys Ile
225                 230                 235

<210> SEQ ID NO 6
<211> LENGTH: 3528
<212> TYPE: DNA
<213> ORGANISM: Staphylococcus epidermidis

<400> SEQUENCE: 6
ttatattttt taacattac gtactgaagc gaaacaattt tcgccattct taaagtaaac      60
aatacgttct tttgagtcaa tagattcaat attatgcctg tttattacaa aactgttatg    120
acatctaaag aaacgttcat caagctgtgc taattccttt aaatttccat aaaattcaat    180
ttgtcgatta tcaagatgtg caatgagtct atgagatttc gtagatgatt caaaaaacat    240
aatatcatca tattgaacgt atactgaatt acttccccgc tttaactcaa tcgtatctac    300
attactttct tttgataata atttgagtct tgtatgtgct gtttcaagac aatctatgat    360
tctcattttt aattcagatg gatcatcttt aaaaataaaa tccatagcag ccactttata    420

-continued

```
aacaaacgtc aaataagtca gctcactgtg actggttaca aatataatat taccaacagg    480
atcatgttta cgaatttcac tggctaattt aataccgttc atatcagctt ctaattgaat    540
atcaaggaag taacaaccaa tgtcattaag ttcttttgat tgctctaaga cctcataagg    600
atcatttgtt cgtaaagcta actccattgg cttttcttca atcattatgt agtttttaat    660
gattgatacc atatgttctc tttgtctttg gtcatcttca caaacaaaaa ttttcattta    720
attctacaca tccttatgat tccttattat ttatttctac tttttgtaca aagtaaccat    780
tttcgatgac agtatctaat aaaacattct cgtttgagtc tgtcagttct tttaaagttg    840
ataaacctaa accgcgatta tcacctttag tagaaaaacc ttgttcaaac aactcatgaa    900
ttttagggat atcattacta catttattca aacgataaa agtgacagat tcctcattat    960
cgatgaatgc gatattgatg agtggttcct caagattttc tgaagcttca atagcattat   1020
caactataat accgataata cgactaagct caacagtatt catatcgata cgatcaattt   1080
catcaggaac ctcaatacta attggaatac gttttcttg agcttgaata attttagtag    1140
taatcagccc tttaatttct ctcactttca acttttcaat accattcatt ttaatagagc   1200 gagttttaa tttatctttc attggaacga tattttcatt aaaatattta cgtaatccag    1260
gcatatcatc ttctctaatg taatctgaaa gagtggtgag gatattcaca taatcatgtc    1320
ggaacttacg catttcattg ttaatgcttt ctatacgtaa cgtgtactca taatatgctt    1380
cgatttcttt tacattacgt ttatacctca tttcacggag tgtaaaattg gacatcacta    1440
atatcactac acttaaaaaa accataatac ccaacaataa gatggcatat aatttaaggg    1500
tatcatttcc tcgcatatca gtttgtgaca ccatataaag taaataaat gatatgaaaa    1560 gtactattgt tattatcaat aagtatcttt tattgagtga caagtaggat acttttaatt   1620
tattgaacaa tagttgagtt aaataagcaa taattagagt tatgattaca aaagaggtaa   1680
aatgtattaa ctgtaaagca aatttaaacg gaatataatc ttttatagtc aaatgtatgt    1740
atacagttat gaaattagtt atatataaga tcatagtggt gaataataca actaatattg   1800
aataaagctt tattttgta taaaagaaaa tggtgattat tataaccaaa actattaatg   1860
ctttactttg ccaaaagtaa tacattattg cagaagggat tacaatcgta aaaacgatta    1920
tgtaatccct aaaattaaat ttcatattaa tgataacttt agtaacccaa atcattaaaa   1980
agatttgtag gcctgcaaac ggaaatagat taatatcatc catatcttac acactttcta   2040
gggttatatt tactcgtata gtttagtcag ttcttctggt acttctggtt cgtcaaagta   2100
agaggcacat acactatctc ctgctacagt accaataaat tccaagattg tagtgaaaaa   2160
ttttataaat aaattaaaaa tgatttccat gattaatatc ctccttaggg aaaaagatgg   2220
gtagtaatgt taaagattct aaaattacac cgaataaaat aagtttattt accggttctt    2280
tagttactaa tgaaataact acgatagtac aatataaaaa tatggagagt attttttttc   2340
gctttacaag acgtctaggt ataggttgtt tcttagttgc tgcaggtgcg tataaaatgg   2400
taataattaa tccgactaat gccatagata aagaacaaa atagttaata tctaacttta    2460
ttattaagta tggaaagata ataagaaaa ttatgttctg aatatgacat aacaatgacg    2520
aatttgcatg cgtaccgtgt gcatgtctcc taattaaaaa ataacttaaa tgagttaaaa   2580
gtgtgtaaaa gaaagtatga aagattattg ctagcccata cacaactata gacttttcaa   2640
tatttatcgc tagtacctgc atccctaaac gaattttag aaactgtatg tgatctaagt    2700 tattttttacg tacgttgtaa atatgagcaa attgctcaat ttttttatcg atgattttca    2760
cttgtttact actctcctca agtgtcatta tacaattttg cgcaacattt tttagaaagc   2820
```

```
atgcctaact gttaaaaaaa tatacctaag tgttttaatt aagtactatt agatatttta    2880
ccatatttag ttttacagtt gagtactaaa tattgctatt tacgaaattt taatctttaa    2940
atggaaaaat catgttttaa tagactcata tcacagtgat gtgattgaaa gatagttgaa    3000
aaatttgctt aatctagtcg agtgaatgtt aaattcattc gtatccatta ccttaattcg    3060
aaaggagtga agttataatg gcagcagata tcatttctac aatcggtgat ttagtaaaat    3120
ggattatcga tacagttaat aaattcaaaa ataatttttt gaatgagtct attgtaactt    3180
ttgtaacttt gttttcttcg tataattaat attattagtg agttgttgag ccatcccaac    3240
ttaataattt actaatataa actaagcaag tgagaagcat tgctagtag ctgtagtttc    3300 cttggactca gtgttacgta ttattcttag ctaccttaaa taggtaatta tttctagcat    3360
gtaagctatc gtaaacaaca ttcaatttat catgttaaat agataaattc actaaaaatt    3420
ttttcataat taataacatc cccaaaaaat agattgaaaa ataactgta aaacattcc     3480 cttaataata agttatcaag ccgtgagtct ctcccaagct cacggctt                3528

<210> SEQ ID NO 7
<211> LENGTH: 561
<212> TYPE: DNA
<213> ORGANISM: Staphylococcus epidermidis
<220> FEATURE:
<223> OTHER INFORMATION: RNAIII

<400> SEQUENCE: 7
atatcacagt gatgtgattg aaagatagtt gaaaaatttg cttaatctag tcgagtgaat     60
gttaaattca ttcgtatcca ttaccttaat tcgaaaggag tgaagttata atggcagcag    120
atatcatttc tacaatcggt gatttagtaa aatggattat cgatacagtt aataaaattca   180 aaaaataatt tttgaatgag tctattgtaa cttttgtaac tttgttttct tcgtataatt    240
aatattatta gtgagttgtt gagccatccc aacttaataa tttactaata taaactaagc    300
aagtgagaag catttgctag tagctgtagt tccttggac tcagtgttac gtattattct    360 tagctaccttaaataggtaattatttctagcatgtaagctatcgtaaacaacattcaatt       420 tatcatgtta aatagataaa ttcactaaaa attttttcat aattaataac atccccaaaa    480
aatagattga aaaataact gtaaaaacat tcccttaata ataagttatc aagccgtgag    540
tctctcccaa gctcacggct t                                             561

<210> SEQ ID NO 8
<211> LENGTH: 25
<212> TYPE: PRT
<213> ORGANISM: Staphylococcus epidermidis
<220> FEATURE:
<223> OTHER INFORMATION: hld

<400> SEQUENCE: 8

Met Ala Ala Asp Ile Ile Ser Thr Ile Gly Asp Leu Val Lys Trp Ile
 1               5                  10                  15

Ile Asp Thr Val Asn Lys Phe Lys Lys
            20                  25

<210> SEQ ID NO 9
<211> LENGTH: 3523
<212> TYPE: DNA
<213> ORGANISM: Staphylococcus epidermidis

<400> SEQUENCE: 9
```

-continued

| | | | | | |
|---|---|---|---|---|---|
| aagccgtgag | cttgggagag | actcacggct | tgataactta | ttattaaggg | aatgttttta | 60 |
| cagttatttt | ttcaatctat | tttttgggga | tgttattaat | tatgaaaaaa | ttttagtgaa | 120 |
| tttatctatt | taacatgata | aattgaatgt | tgtttacgat | agcttacatg | ctagaaataa | 180 |
| ttacctattt | aaggtagcta | agaataatac | gtaacactga | gtccaaggaa | actacagcta | 240 |
| ctagcaaatg | cttctcactt | gcttagttta | tattagtaaa | ttattaagtt | gggatggctc | 300 |
| aacaactcac | taatagtatt | aattatacga | agaaaacaaa | gttacaaaag | ttacaataaa | 360 |
| ctcattcaaa | aattattttt | tgaatttatt | aactgtatcg | ataatccatt | ttactaaatc | 420 |
| accgattgta | gaaatgatat | ctgctgccat | tataacttca | ctcctttcga | attaaggtaa | 480 |
| tggatacgaa | tgaatttaac | attcactcga | ctagattaag | caaattttc | aactatcttt | 540 |
| caatcacatc | tctgtgatat | gagtctatta | aaacatgatt | tttccattta | aagattaaaa | 600 |
| tttcgtaaat | agcaatattt | agtactcaac | tgtaaaacta | aatatggtaa | aatatctaat | 660 |
| agcacttaat | taaaacactt | aggtatattt | ttttaacagt | taggcatgct | ttctaaaaaa | 720 |
| tgttgcgcaa | aattgtataa | tgacacctga | ggagagtagt | aacaagtgaa | atcatcgat | 780 |
| aaaaaaattg | agcaatttgc | tcaatatttg | caacgtaaaa | ataacttaga | tcacatacag | 840 |
| ttttttgaaaa | ttcgtctagg | aatgcaggta | ctagcaataa | atattgaaaa | gtctatagtt | 900 |
| gtgtatgggc | tagcaataat | ctttcatact | ttcttttaca | cacttttaac | tcatttaagt | 960 |
| tattttttaa | ttaggagaca | tgcacacggt | acacatgcaa | attcgtcatt | gttatgtcat | 1020 |
| attcagaaca | taattttctt | tattattttt | ccatacttaa | taataaagtt | agatattaac | 1080 |
| tattttgttc | ttttatctgt | ggcattagtc | ggattaatta | ttaccatttt | atacgcacct | 1140 |
| gcagcaacta | agaaacaacc | tatacctaga | cgtcttgtaa | agcgaaaaaa | aatactctcc | 1200 |
| atattttat | attgtactat | cgtagttatt | tcattattaa | ctaaagaacc | ggtaaataaa | 1260 |
| cttattttat | tcggtgtaat | tttagaatct | ttaacattac | tacccatctt | tttccctaag | 1320 |
| gaggatatta | atcatggaaa | acattttttaa | tttatttata | aaattttttca | ctacaatctt | 1380 |
| ggaatttatt | ggtactgtag | caggagatag | tgtatgtgct | tcttactttg | acgaaccaga | 1440 |
| agtgccagaa | gaactgacta | aactatacga | gtaaatataa | ccctagaaag | tgtgtaagat | 1500 |
| atggatgata | ttaatttatt | tccgtttgca | ggcctacaaa | tcttttttaat | gatttgggtt | 1560 |
| actaaagtta | tcattaatat | gaaatttaat | tttagggatt | acataatcgt | ttttacgatt | 1620 |
| gtaatcccctt | ctgctataat | gtattacttt | tggcaaagta | aagcattaat | agttttggtt | 1680 |
| ataataatca | tcattttctt | ttatacaaaa | ataaaacttt | attcaatatt | agttgtatta | 1740 |
| ttcacgacta | tgatcttata | tataactaat | ttcataactg | tatacataca | tttaactata | 1800 |
| aaagattata | ttccgtttaa | atttgttttta | cagttaatac | atttttacctt | ttttgtaatc | 1860 |
| ataactctaa | tcattgctta | tttaactcaa | ctattgttca | ataaattaaa | agtatccctat | 1920 |
| ttgtcactca | ataaaagata | cttattcata | taacaattg | tactttttat | atcatttatt | 1980 |
| ttactttata | tggtgtcaca | aactgatatg | cgaggaaatg | atacacttaa | attatatgcc | 2040 |
| atcttgttga | tgggtattat | ggttttttta | agtgtagtga | ttttagtgat | gtccaatttt | 2100 |
| acacttcgtg | aaatgaggta | taacgtaat | gtaaaagaaa | tcgaagcata | ttatgaatac | 2160 |
| acgttacgta | tagaaagcat | taacaatgaa | atgcgtaagt | tccggcatga | ttatgtgaat | 2220 |
| atcctcacca | ctctttcaga | ttacataaga | gaagatgata | tgcctggatt | acgtaaaatat | 2280 |
| tttaatgaaa | atatcgttcc | aatgaaagat | aaattaaaaa | ctcgctctat | taaaatgaat | 2340 |
| ggtattgaaa | agttgaaagt | gagagaaatt | aaagggttga | ttactactaa | aattattcaa | 2400 |

-continued

```
gctcaagaaa aacgtattcc aattagtatt gaggttcctg atgaaattga tcgtatcgat    2460
atgaatactg ttgagcttag tcgtattatc ggtattatag ttgataatgc aattgaagct    2520
tcagaaaatc ttgaggaacc actcatcaat atcgcattca tcgataatga ggaatctgtc    2580
acttttatcg ttatgaataa atgtagtgat gatatcccta aaattcatga gttgtttgaa    2640
caaggttttt ctactaaagg tgataatcgc ggtttaggtt tatcaacttt aaaagaactg    2700
acagactcaa acgagaatgt tttattagat actgtcatcg aaaatggtta ctttgtacaa    2760
aaagtagaaa taaataataa ggaatcataa ggatgtgtag aattaaatga aaattttgt     2820 ttgtgaagat gaccaaagac aaagagaaca tatggtatca atcattaaaa actacataat    2880
gattgaagaa aagccaatgg agttagcctt agcaacaaat gatccttatg aggtcttaga    2940
gcaatcaaaa gaacttaatg acattggttg ttacttcctt gatattcaat agaagctga    3000 tatgaacggt attaaattag ccagtgaaat tcgtaaacat gatcctgttg gtaatattat    3060
atttgtaacc agtcacagtg aactgactta tttgacgttt gtttataaag tggctgctat    3120
ggattttatt tttaaggatg atccatctga attaaaaatg agaatcatag attgtcttga    3180
aacagcacat acacgactca aattattatc aaaagaaagt aatgtagata cgattgagtt    3240
aaagcgggga agtaattcag tatacgttca atatgatgat attatgtttt ttgaatcatc    3300
tacgaaatct catagactca tcgcacatct tgataatcgg caaattgaat tttatggaaa    3360 tttaaggaa ttagcacagc ttgatgaacg tttctttaga tgtcataaca gttttgtgat    3420
aaacaggcat aatattgaat ctattgactc aaaagaacgt attgtttact ttaagaatgg    3480
cgaaaattgt ttcgcttcag tacgtaatgt taaaaaaata taa                      3523
```

<210> SEQ ID NO 10
<211> LENGTH: 194
<212> TYPE: PRT
<213> ORGANISM: Staphylococcus epidermidis
<220> FEATURE:
<223> OTHER INFORMATION: agrB
<221> NAME/KEY: VARIANT
<222> LOCATION: (1)
<223> OTHER INFORMATION: nucleic acid triplet 'gtg' codes for amino acid 'MET'

<400> SEQUENCE: 10

```
Met Lys Ile Ile Asp Lys Lys Ile Glu Gln Phe Ala Gln Tyr Leu Gln
 1               5                  10                  15

Arg Lys Asn Asn Leu Asp His Ile Gln Phe Leu Lys Ile Arg Leu Gly
            20                  25                  30

Met Gln Val Leu Ala Ile Asn Ile Glu Lys Ser Ile Val Val Tyr Gly
        35                  40                  45

Leu Ala Ile Ile Phe His Thr Phe Phe Tyr Thr Leu Leu Thr His Leu
    50                  55                  60

Ser Tyr Phe Leu Ile Arg Arg His Ala His Gly Thr His Ala Asn Ser
65                  70                  75                  80

Ser Leu Leu Cys His Ile Gln Asn Ile Ile Phe Phe Ile Ile Phe Pro
                85                  90                  95

Tyr Leu Ile Ile Lys Leu Asp Ile Asn Tyr Phe Val Leu Leu Ser Val
            100                 105                 110

Ala Leu Val Gly Leu Ile Ile Thr Ile Leu Tyr Ala Pro Ala Ala Thr
        115                 120                 125

Lys Lys Gln Pro Ile Pro Arg Arg Leu Val Lys Arg Lys Ile Leu
    130                 135                 140
```

```
Ser Ile Phe Leu Tyr Cys Thr Ile Val Val Ile Ser Leu Leu Thr Lys
145                 150                 155                 160

Glu Pro Val Asn Lys Leu Ile Leu Phe Gly Val Ile Leu Glu Ser Leu
                165                 170                 175

Thr Leu Leu Pro Ile Phe Phe Pro Lys Glu Asp Ile Asn His Gly Lys
            180                 185                 190

His Phe
```

<210> SEQ ID NO 11
<211> LENGTH: 46
<212> TYPE: PRT
<213> ORGANISM: Staphylococcus epidermidis
<220> FEATURE:
<223> OTHER INFORMATION: agrD

<400> SEQUENCE: 11

```
Met Glu Asn Ile Phe Asn Leu Phe Ile Lys Phe Phe Thr Thr Ile Leu
1               5                   10                  15

Glu Phe Ile Gly Thr Val Ala Gly Asp Ser Val Cys Ala Ser Tyr Phe
                20                  25                  30

Asp Glu Pro Glu Val Pro Glu Glu Leu Thr Lys Leu Tyr Glu
            35                  40                  45
```

<210> SEQ ID NO 12
<211> LENGTH: 429
<212> TYPE: PRT
<213> ORGANISM: Staphylococcus epidermidis
<220> FEATURE:
<223> OTHER INFORMATION: agrC

<400> SEQUENCE: 12

```
Met Asp Asp Ile Asn Leu Phe Pro Phe Ala Gly Leu Gln Ile Phe Leu
1               5                   10                  15

Met Ile Trp Val Thr Lys Val Ile Ile Asn Met Lys Phe Asn Phe Arg
                20                  25                  30

Asp Tyr Ile Ile Val Phe Thr Ile Val Ile Pro Ser Ala Ile Met Tyr
            35                  40                  45

Tyr Phe Trp Gln Ser Lys Ala Leu Ile Val Leu Val Ile Ile Ile
    50                  55                  60

Ile Phe Phe Tyr Thr Lys Ile Lys Leu Tyr Ser Ile Leu Val Val Leu
65                  70                  75                  80

Phe Thr Thr Met Ile Leu Tyr Ile Thr Asn Phe Ile Thr Val Tyr Ile
                85                  90                  95

His Leu Thr Ile Lys Asp Tyr Ile Pro Phe Lys Phe Val Leu Gln Leu
            100                 105                 110

Ile His Phe Thr Phe Phe Val Ile Ile Thr Leu Ile Ile Ala Tyr Leu
    115                 120                 125

Thr Gln Leu Leu Phe Asn Lys Leu Lys Val Ser Tyr Leu Ser Leu Asn
130                 135                 140

Lys Arg Tyr Leu Phe Ile Ile Thr Ile Val Leu Phe Ile Ser Phe Ile
145                 150                 155                 160

Leu Leu Tyr Met Val Ser Gln Thr Asp Met Arg Gly Asn Asp Thr Leu
                165                 170                 175

Lys Leu Tyr Ala Ile Leu Leu Met Gly Ile Met Val Phe Leu Ser Val
            180                 185                 190

Val Ile Leu Val Met Ser Asn Phe Thr Leu Arg Glu Met Arg Tyr Lys
    195                 200                 205
```

```
Arg Asn Val Lys Glu Ile Glu Ala Tyr Tyr Glu Tyr Thr Leu Arg Ile
    210                 215                 220

Glu Ser Ile Asn Asn Glu Met Arg Lys Phe Arg His Asp Tyr Val Asn
225                 230                 235                 240

Ile Leu Thr Thr Leu Ser Asp Tyr Ile Arg Glu Asp Met Pro Gly
                245                 250                 255

Leu Arg Lys Tyr Phe Asn Glu Asn Ile Val Pro Met Lys Asp Lys Leu
                260                 265                 270

Lys Thr Arg Ser Ile Lys Met Asn Gly Ile Glu Lys Leu Lys Val Arg
            275                 280                 285

Glu Ile Lys Gly Leu Ile Thr Thr Lys Ile Ile Gln Ala Gln Glu Lys
290                 295                 300

Arg Ile Pro Ile Ser Ile Glu Val Pro Asp Glu Ile Asp Arg Ile Asp
305                 310                 315                 320

Met Asn Thr Val Glu Leu Ser Arg Ile Ile Gly Ile Ile Val Asp Asn
                325                 330                 335

Ala Ile Glu Ala Ser Glu Asn Leu Glu Glu Pro Leu Ile Asn Ile Ala
                340                 345                 350

Phe Ile Asp Asn Glu Glu Ser Val Thr Phe Ile Val Met Asn Lys Cys
                355                 360                 365

Ser Asp Asp Ile Pro Lys Ile His Glu Leu Phe Glu Gln Gly Phe Ser
370                 375                 380

Thr Lys Gly Asp Asn Arg Gly Leu Gly Leu Ser Thr Leu Lys Glu Leu
385                 390                 395                 400

Thr Asp Ser Asn Glu Asn Val Leu Leu Asp Thr Val Ile Glu Asn Gly
                405                 410                 415

Tyr Phe Val Gln Lys Val Glu Ile Asn Asn Lys Glu Ser
                420                 425

<210> SEQ ID NO 13
<211> LENGTH: 238
<212> TYPE: PRT
<213> ORGANISM: Staphylococcus epidermidis
<220> FEATURE:
<223> OTHER INFORMATION: agrA

<400> SEQUENCE: 13

Met Lys Ile Phe Val Cys Glu Asp Asp Gln Arg Gln Arg Glu His Met
1               5                   10                  15

Val Ser Ile Ile Lys Asn Tyr Ile Met Ile Glu Glu Lys Pro Met Glu
                20                  25                  30

Leu Ala Leu Ala Thr Asn Asp Pro Tyr Glu Val Leu Glu Gln Ser Lys
            35                  40                  45

Glu Leu Asn Asp Ile Gly Cys Tyr Phe Leu Asp Ile Gln Leu Glu Ala
        50                  55                  60

Asp Met Asn Gly Ile Lys Leu Ala Ser Glu Ile Arg Lys His Asp Pro
65                  70                  75                  80

Val Gly Asn Ile Ile Phe Val Thr Ser His Ser Glu Leu Thr Tyr Leu
                85                  90                  95

Thr Phe Val Tyr Lys Val Ala Ala Met Asp Phe Ile Phe Lys Asp Asp
                100                 105                 110

Pro Ser Glu Leu Lys Met Arg Ile Ile Asp Cys Leu Glu Thr Ala His
            115                 120                 125

Thr Arg Leu Lys Leu Leu Ser Lys Glu Ser Asn Val Asp Thr Ile Glu
130                 135                 140
```

-continued

```
Leu Lys Arg Gly Ser Asn Ser Val Tyr Val Gln Tyr Asp Asp Ile Met
145                 150                 155                 160

Phe Phe Glu Ser Ser Thr Lys Ser His Arg Leu Ile Ala His Leu Asp
            165                 170                 175

Asn Arg Gln Ile Glu Phe Tyr Gly Asn Leu Lys Glu Leu Ala Gln Leu
        180                 185                 190

Asp Glu Arg Phe Phe Arg Cys His Asn Ser Phe Val Ile Asn Arg His
    195                 200                 205

Asn Ile Glu Ser Ile Asp Ser Lys Glu Arg Ile Val Tyr Phe Lys Asn
    210                 215                 220

Gly Glu Asn Cys Phe Ala Ser Val Arg Asn Val Lys Lys Ile
225                 230                 235
```

<210> SEQ ID NO 14
<211> LENGTH: 3523
<212> TYPE: DNA
<213> ORGANISM: Staphylococcus epidermidis

<400> SEQUENCE: 14

| | | | | | |
|---|---|---|---|---|---|
| ttatatttttt | taacattac | gtactgaagc | gaaacaattt | tcgccattct | taaagtaaac | 60 |
| aatacgttct | tttgagtcaa | tagattcaat | attatgcctg | tttatcacaa | aactgttatg | 120 |
| acatctaaag | aaacgttcat | caagctgtgc | taattccttt | aaatttccat | aaaattcaat | 180 |
| ttgccgatta | tcaagatgtg | cgatgagtct | atgagatttc | gtagatgatt | caaaaaacat | 240 |
| aatatcatca | tattgaacgt | atactgaatt | acttccccgc | tttaactcaa | tcgtatctac | 300 |
| attactttct | tttgataata | atttgagtcg | tgtatgtgct | gtttcaagac | aatctatgat | 360 |
| tctcattttt | aattcagatg | gatcatcctt | aaaaataaaa | tccatagcag | ccactttata | 420 |
| aacaaacgtc | aaataagtca | gttcactgtg | actggttaca | aatataatat | taccaacagg | 480 |
| atcatgttta | cgaatttcac | tggctaattt | aataccgttc | atatcagctt | ctaattgaat | 540 |
| atcaaggaag | taacaaccaa | tgtcattaag | ttcttttgat | tgctctaaga | cctcataagg | 600 |
| atcatttgtt | gctaaggcta | actccattgg | cttttcttca | atcattatgt | agtttttaat | 660 |
| gattgatacc | atatgttctc | tttgtctttg | gtcatcttca | caaacaaaaa | ttttcattta | 720 |
| attctacaca | tccttatgat | tccttattat | ttatttctac | tttttgtaca | aagtaaccat | 780 |
| tttcgatgac | agtatctaat | aaaacattct | cgtttgagtc | tgtcagttct | tttaaagttg | 840 |
| ataaacctaa | accgcgatta | tcacctttag | tagaaaaacc | ttgttcaaac | aactcatgaa | 900 |
| ttttagggat | atcatcacta | catttattca | taacgataaa | agtgacagat | tcctcattat | 960 |
| cgatgaatgc | gatattgatg | agtggttcct | caagattttc | tgaagcttca | attgcattat | 1020 |
| caactataat | accgataata | cgactaagct | caacagtatt | catatcgata | cgatcaattt | 1080 |
| catcaggaac | ctcaatacta | attggaatac | gttttctctg | agcttgaata | attttagtag | 1140 |
| taatcaaccc | tttaatttct | ctcactttca | acttttcaat | accattcatt | taatagagc | 1200 |
| gagttttta a| tttatctttc | attggaacga | tattttcatt | aaaatattta | cgtaatccag | 1260 |
| gcatatcatc | ttctcttatg | taatctgaaa | gagtggtgag | gatattcaca | taatcatgcc | 1320 |
| ggaacttacg | catttcattg | ttaatgcttt | ctatacgtaa | cgtgtattca | taatatgctt | 1380 |
| cgatttcttt | tacattacgt | ttatacctca | tttcacgaag | tgtaaaattg | gacatcacta | 1440 |
| aaatcactac | acttaaaaaa | accataatac | ccatcaacaa | gatggcatat | aatttaagtg | 1500 |
| tatcatttcc | tcgcatatca | gtttgtgaca | ccatataaag | taaaataaat | gatataaaaa | 1560 |

```
gtacaattgt tattatgaat aagtatcttt tattgagtga caaataggat acttttaatt    1620
tattgaacaa tagttgagtt aaataagcaa tgattagagt tatgattaca aaaaaggtaa    1680
aatgtattaa ctgtaaaaca aatttaaacg aatataatc ttttatagtt aaatgtatgt    1740
atacagttat gaaattagtt atatataaga tcatagtcgt gaataataca actaatattg    1800
aataaagttt tatttttgta taaaagaaaa tgatgattat tataaccaaa actattaatg    1860
ctttactttg ccaaaagtaa tacattatag cagaagggat tacaatcgta aaaacgatta    1920
tgtaatccct aaaattaaat ttcatattaa tgataacttt agtaacccaa atcattaaaa    1980
agatttgtag gcctgcaaac ggaaataaat taatatcatc catatcttac acactttcta    2040
gggttatatt tactcgtata gtttagtcag ttcttctggc acttctggtt cgtcaaagta    2100
agaagcacat acactatctc ctgctacagt accaataaat tccaagattg tagtgaaaaa    2160
ttttataaat aaattaaaaa tgttttccat gattaatatc ctccttaggg aaaaagatgg    2220
gtagtaatgt taaagattct aaaattacac cgaataaaat aagtttattt accggttctt    2280
tagttaataa tgaaataact acgatagtac aatataaaaa tatggagagt attttttttc    2340
gctttacaag acgtctaggt ataggttgtt tcttagttgc tgcaggtgcg tataaaatgg    2400
taataattaa tccgactaat gccacagata aagaacaaa atagttaata tctaacttta     2460
ttattaagta tggaaaaata ataagaaaaa ttatgttctg aatatgacat aacaatgacg    2520
aatttgcatg tgtaccgtgt gcatgtctcc taattaaaaa ataacttaaa tgagttaaaa    2580
gtgtgtaaaa gaaagtatga aagattattg ctagcccata cacaactata gacttttcaa    2640
tatttattgc tagtacctgc attcctagac gaattttcaa aaactgtatg tgatctaagt    2700 tattttttacg ttgtaaatat tgagcaaatt gctcaatttt tttatcgatg attttcactt    2760
gttactactc tcctcaggtg tcattataca attttgcgca acatttttta gaaagcatgc    2820
ctaactgtta aaaaaatata cctaagtgtt ttaattaagt gctattagat attttaccat    2880
atttagtttt acagttgagt actaaatatt gctatttacg aaattttaat ctttaaatgg    2940
aaaaatcatg ttttaataga ctcatatcac agagatgtga ttgaaagata gttgaaaaat    3000
ttgcttaatc tagtcgagtg aatgttaaat tcattcgtat ccattacctt aattcgaaag    3060
gagtgaagtt ataatggcag cagatatcat ttctacaatc ggtgatttag taaaatggat    3120
tatcgataca gttaataaat tcaaaaaata atttttgaat gagtttattg taacttttgt    3180
aactttgttt tcttcgtata attaatacta ttagtgagtt gttgagccat cccaacttaa    3240
taatttacta atataaacta agcaagtgag aagcatttgc tagtagctgt agtttccttg    3300
gactcagtgt tacgtattat tcttagctac cttaaatagg taattattc tagcatgtaa    3360 gctatcgtaa acaacattca atttatcatg ttaaatagat aaattcacta aaattttttc    3420
ataattaata acatccccaa aaaatagatt gaaaaaataa ctgtaaaaac attcccttaa    3480
taataagtta tcaagccgtg agtctctccc aagctcacgg ctt                      3523
```

<210> SEQ ID NO 15
<211> LENGTH: 560
<212> TYPE: DNA
<213> ORGANISM: Staphylococcus epidermidis
<220> FEATURE:
<223> OTHER INFORMATION: RNAIII

<400> SEQUENCE: 15

```
atatcacaga gatgtgattg aaagatagtt gaaaaatttg cttaatctag tcgagtgaat      60
gttaaattca ttcgtatcca ttaccttaat tcgaaggag tgaagttata atggcagcag       120
```

```
atatcatttc tacaatcggt gatttagtaa aatggattat cgatacagtt aataaattca      180
aaaaataatt tttgaatgag tttattgtaa cttttgtaac tttgttttct tcgtataatt      240
aatactatta gtgagttgtt gagccatccc aacttaataa tttactaata taaactaagc      300
aagtgagaag catttgctag tagctgtagt ttccttggac tcagtgttac gtattattct      360
tagctacctt aaataggtaa ttatttctag catgtaagct atcgtaaaca acattcaatt      420
tatcatgtta aatagataaa ttcactaaaa ttttttcata attaataaca tccccaaaaa      480
atagattgaa aaaataactg taaaaacatt cccttaataa taagttatca agccgtgagt      540
ctctcccaag ctcacggctt                                                  560
```

<210> SEQ ID NO 16
<211> LENGTH: 25
<212> TYPE: PRT
<213> ORGANISM: Staphylococcus epidermidis
<220> FEATURE:
<223> OTHER INFORMATION: hld

<400> SEQUENCE: 16

Met Ala Ala Asp Ile Ile Ser Thr Ile Gly Asp Leu Val Lys Trp Ile
 1               5                  10                  15

Ile Asp Thr Val Asn Lys Phe Lys Lys
            20                  25

<210> SEQ ID NO 17
<211> LENGTH: 9
<212> TYPE: PRT
<213> ORGANISM: Staphylococcus epidermidis
<220> FEATURE:
<221> NAME/KEY: VARIANT
<222> LOCATION: (5)
<223> OTHER INFORMATION: C-terminal cyclized through thioester linkage
      to cystine residue 5

<400> SEQUENCE: 17

Gly Asp Ser Val Xaa Ala Ser Tyr Phe
 1               5

<210> SEQ ID NO 18
<211> LENGTH: 7
<212> TYPE: PRT
<213> ORGANISM: Staphylococcus epidermidis
<220> FEATURE:
<221> NAME/KEY: VARIANT
<222> LOCATION: (3)
<223> OTHER INFORMATION: C-terminal cyclyzed through thioester linkage
      to cystine residue 3

<400> SEQUENCE: 18

Ser Val Xaa Ala Ser Tyr Phe
 1               5

<210> SEQ ID NO 19
<211> LENGTH: 8
<212> TYPE: PRT
<213> ORGANISM: Staphylococcus epidermidis
<220> FEATURE:
<221> NAME/KEY: VARIANT
<222> LOCATION: (4)
<223> OTHER INFORMATION: C-terminal cyclized to Xaa at residue 4 through
      either 1) thioester, 2) amide, 3) ester, or 4)
      methylketo linkages

<400> SEQUENCE: 19

```
-continued

Asp Ser Val Xaa Ala Ser Tyr Phe
 1               5

<210> SEQ ID NO 20
<211> LENGTH: 346
<212> TYPE: DNA
<213> ORGANISM: Staphylococcus epidermidis

<400> SEQUENCE: 20
tcctcaagtg tcattataca attttgcgca acatttttta gaaagcatgc ctaactgtta    60
aaaaaatata cctaagtgtt ttaattaagt actattagat attttaccat atttagtttt   120
acagttgagt actaaatatt gctatttacg aaattttaat ctttaaatgg aaaaatcatg   180
ttttaataga ctcatatcac agtgatgtga ttgaaagata gttgaaaaat ttgcttaatc   240
tagtcgagtg aatgttaaat tcattcgtat ccattacctt aattcgaaag gagtgaagtt   300
ataatggcag cagatatcat ttctacaatc ggtgatttag taaaat              346

<210> SEQ ID NO 21
<211> LENGTH: 10
<212> TYPE: PRT
<213> ORGANISM: Staphylococcus epidermidis

<400> SEQUENCE: 21

Met Thr Phe Asn Ile Ile Lys Leu Glu Asn
 1               5                  10
```